(12) United States Patent
Kordowicz et al.

(10) Patent No.: US 7,049,124 B1
(45) Date of Patent: May 23, 2006

(54) **HYALURONIDASE FROM THE *HIRUDINARIA MANILLENSIS* ISOLATION, PURIFICATION AND RECOMBINANT METHOD OF PRODUCTION**

(75) Inventors: Maria Kordowicz, Griesheim (DE); Detlef Gussow, Darmstadt (DE); Uwe Hofmann, Seeheim (DE); Tadeusz Pacuszka, Warsaw (PL); Andrzej Gardas, Warsaw (PL)

(73) Assignee: Merck Patent GmbH, Darmstadt (DE)

( * ) Notice: Subject to any disclaimer, the term of this patent is extended or adjusted under 35 U.S.C. 154(b) by 495 days.

(21) Appl. No.: 10/009,500

(22) PCT Filed: Jun. 6, 2000

(86) PCT No.: PCT/EP00/05181

§ 371 (c)(1),
(2), (4) Date: Dec. 11, 2001

(87) PCT Pub. No.: WO00/77221

PCT Pub. Date: Dec. 21, 2000

(30) Foreign Application Priority Data

Jun. 12, 1999 (EP) .................................. 99111468

(51) Int. Cl.
| C12N 9/26 | (2006.01) |
| C12N 9/88 | (2006.01) |
| C12N 15/56 | (2006.01) |
| C12N 15/66 | (2006.01) |
| A61K 38/47 | (2006.01) |
| A61K 38/51 | (2006.01) |

(52) U.S. Cl. .................. 435/201; 435/232; 435/320.1; 435/252.3; 424/94.62; 424/94.5; 536/23.2

(58) Field of Classification Search ................ 435/201, 435/232, 320.1, 252.3; 424/94.62, 94.5; 576/23.2
See application file for complete search history.

(56) References Cited

U.S. PATENT DOCUMENTS 5,827,721 A    10/1998 Stern et al.
5,976,841 A *  11/1999 Wnendt et al. ............ 435/69.7

FOREIGN PATENT DOCUMENTS

EP    0 193330 A    9/1986

OTHER PUBLICATIONS

C.P. Jones and R.T. Sawyer: "Heparin Inhibits Mammalian, But Not Leech Hyaluronidase," Thrombin Research, vol. 55, No. 6, 1989, pp. 791-796, XP000953413.

* cited by examiner

*Primary Examiner*—Charles L. Patterson, Jr.
(74) *Attorney, Agent, or Firm*—Millen, White, Zelano & Branigan, P.C.

(57) ABSTRACT

The present invention relates to the isolation, purification and characterization of a hyaluronidase which derives from the tropical leech *Hirudinaria manillensis*. Therefore, according to this invention, the enzyme was called "manillase". The invention is furthermore concerned with the recombinant method of production of manillase which includes the disclosure of DNA and amino acid sequences as well as of expression vectors and host systems. Finally, the invention relates to the use of manillase for therapeutic purposes, for example, for the treatment of myocardial diseases, thrombotic events and tumors.

25 Claims, 20 Drawing Sheets

Figure 1:
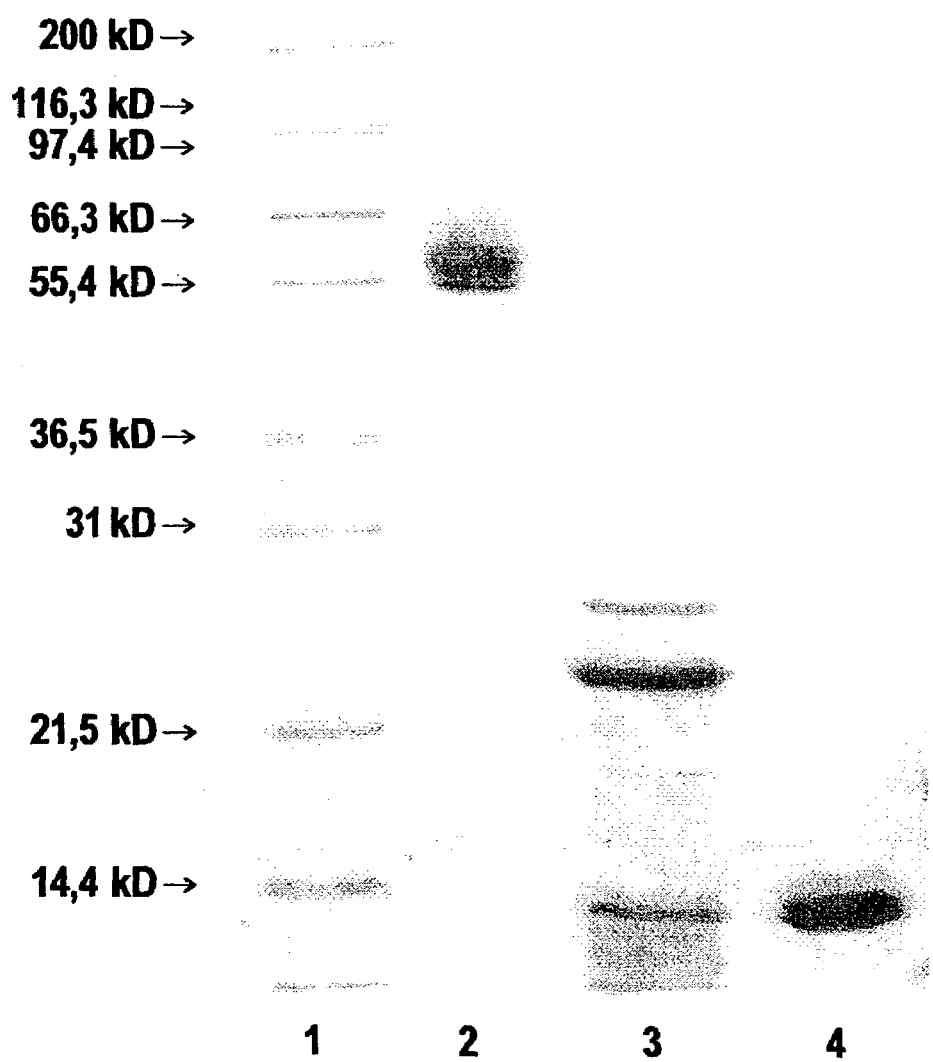

Fig.2
a) - SDS-PAGE
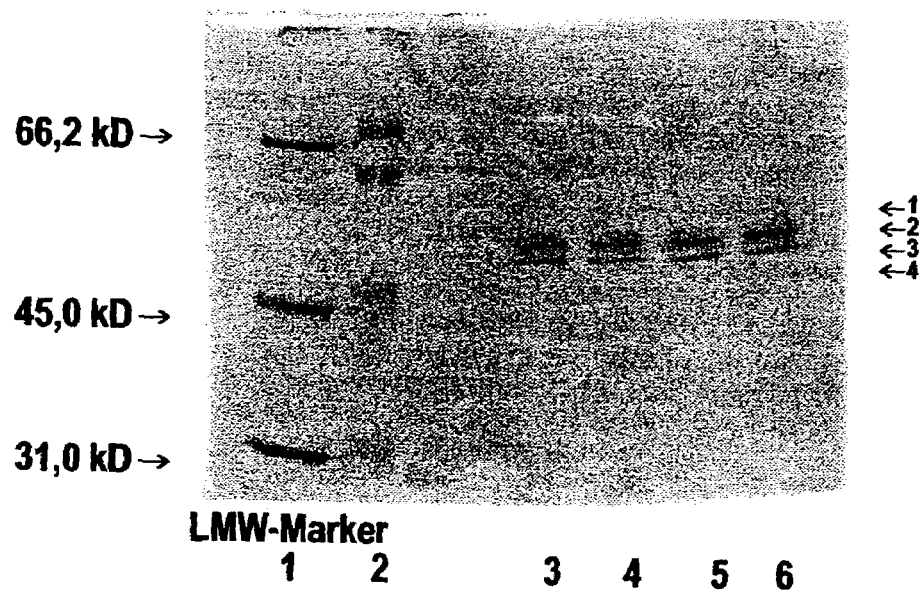
66,2 kD →
45,0 kD →
31,0 kD →
← 1
← 2
← 3
← 4
LMW-Marker
1  2  3  4  5  6
b) - SDS-PAGE-Western blot
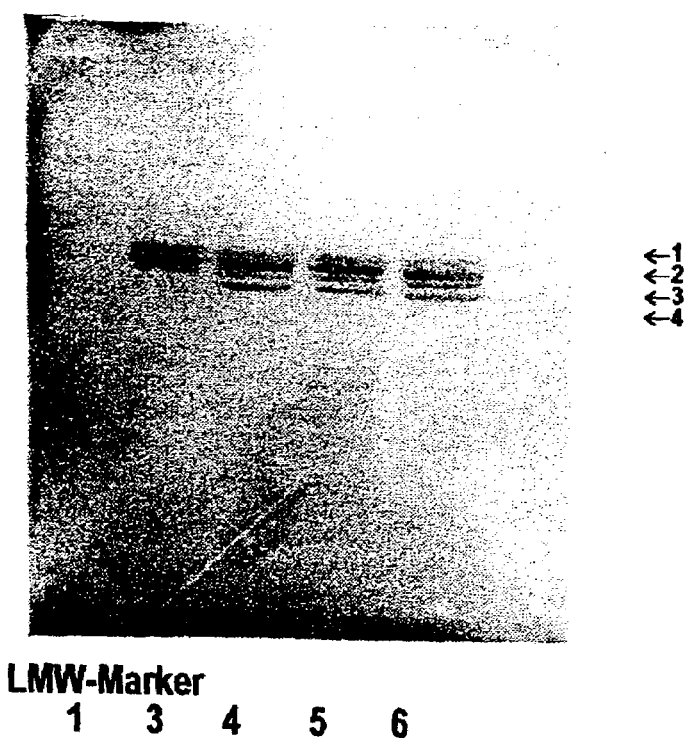
← 1
← 2
← 3
← 4
LMW-Marker
1  3  4  5  6

Fig. 7

```
KEIAVTIDDK  NVIASVSESF  HGVAFDASLF  SPKGLWSFVD  ITSPKLFKLL   50
EGLSPGYFRV  GGTFANWLFF  DLDENNKWKD  YWAFKDKTPE  TATITRRWLF  100
RKQNNLKKET  EDDLVKLTKG  SKMRLLFDLN  AEVRTGYEIG  KKMTSTWDSS  150
EAEKLFKYCV  SKGYGDNIDW  ELGNEPDHTS  AHNLTEKQVG  EDFKALHKVL  200
EKYPTLNKGS  LVGPDVGWMG  VSYVKGLADG  AGDLVTAFTL  HQYYFDGNTS  250
DVSTYLDATY  FKKLQQLFDK  VKDVLKNSQH  KDKPLWLGET  SSGYNSGTKD  300
VSDRYVSGFL  TLDKLGLSAA  NNVKVVIRQT  IYNGYYGLLD  KNTLEPNPDY  350
WLMHVHNSLV  GNTVFKVDVS  DPTNKARVYA  QCTKTNSKHT  QSRYYKGSLT  400
IFALNVGDED  VTLKIDQYGG  KKIYSYILTP  EGGQLTSQKV  LLNGKELKLV  450
SDQLPELNAN  ESKTSFTLSP  KTFGFFVVSD  ANVEACKK               488
```

Fig. 8:

| | | | | | | | | | | | |
|---|---|---|---|---|---|---|---|---|---|---|---|
| AAA | GAG | ATT | GCC | GTG | ACA | ATT | GAC | GAT | AAG | AAT | GTG |
| K | E | I | A | V | T | I | D | D | K | N | V |
| ATT | GCA | TCT | GCC | AGT | GGG | TCT | TTC | CTT | GGA | GTT | GCC |
| I | A | S | A | S | G | S | F | L | G | V | A |
| TTT | GAT | GCG | TCT | CTA | TTT | TCG | CCC | AAG | GGT | CTT | TGG |
| F | D | A | S | L | F | S | P | K | G | L | W |
| AGC | TTT | GTT | GAT | ATT | ACC | TCT | CCA | AAA | TTG | TTC | AAA |
| S | F | V | D | I | T | S | P | K | L | F | K |
| TTG | CTG | GAA | GGA | CTT | TCT | CCT | GGA | TAC | TTC | AGG | GTT |
| L | L | E | G | L | S | P | G | Y | F | R | V |
| GGC | GGA | ACG | TTT | GCC | AAT | TGG | CTG | TTT | TTT | GAC | TTG |
| G | G | T | F | A | N | W | L | F | F | D | L |
| GAC | GAA | AAT | AAT | AAG | TGG | AAG | GAT | TAT | TGG | GCT | TTT |
| D | E | N | N | K | W | K | D | Y | W | A | F |
| AAA | GAC | AAA | ACC | CCC | GAA | ACT | GCG | ACA | ATA | ACA | AGG |
| K | D | K | T | P | E | T | A | T | I | T | R |
| AGA | TGG | CTG | TTC | AGA | AAA | CAA | AAT | AAT | CTG | AAA | AAG |
| R | W | L | F | R | K | Q | N | N | L | K | K |
| GAG | ACT | TTT | GAC | AAT | TTA | GTG | AAA | CTA | ACA | AAG | GGA |
| E | T | F | D | N | L | V | K | L | T | K | G |
| AGC | AAG | ATG | AGA | TTG | TTA | TTC | GAT | TTG | AAT | GCC | GAA |
| S | K | M | R | L | L | F | D | L | N | A | E |
| GTG | AGG | ACT | GGT | TAT | GAA | ATT | GGA | AAG | AAG | ATG | ACA |
| V | R | T | G | Y | E | I | G | K | K | M | T |
| TCC | ACT | TGG | GAT | TCA | TCG | GAG | GCT | GAA | AAG | TTA | TTT |
| S | T | W | D | S | S | E | A | E | K | L | F |
| AAA | TAT | TGT | GTG | TCA | AAA | GGT | TAC | GGA | GAC | AAT | ATC |
| K | Y | C | V | S | K | G | Y | G | D | N | I |
| GAT | TGG | GAA | CTT | GGA | AAT | GAA | CCG | GAC | CAC | ACC | TCA |
| D | W | E | L | G | N | E | P | D | H | T | S |
| GCT | CAC | AAT | TTA | ACT | GAA | AAG | CAG | GTT | GGA | GAA | GAT |
| A | H | N | L | T | E | K | Q | V | G | E | D |
| TTT | AAA | GCA | CTG | CAT | AAA | GTT | CTA | GAG | AAA | TAT | CCA |
| F | K | A | L | H | K | V | L | E | K | Y | P |

Fig 8 (contnd)

| | | | | | | | | | | | |
|---|---|---|---|---|---|---|---|---|---|---|---|
| ACT<br>T | CTT<br>L | AAC<br>N | AAG<br>K | GGA<br>G | TCG<br>S | CTC<br>L | GTT<br>V | GGT<br>G | CCA<br>P | GAT<br>D | GTA<br>V |
| GGG<br>G | TGG<br>W | ATG<br>M | GGC<br>G | GTC<br>V | AGT<br>S | WAC<br>Y | GTC<br>V | AAG<br>K | GGA<br>G | TTG<br>L | GCA<br>A |
| GAC<br>D | GAG<br>E | GCR<br>A | GGT<br>G | GAC<br>D | CAT<br>H | GTA<br>V | ACK<br>T | GCT<br>A | TTT<br>F | ACA<br>T | CTC<br>L |
| CAC<br>H | CAA<br>Q | TAT<br>Y | TAT<br>Y | TTC<br>F | GAT<br>D | GGA<br>G | AAC<br>N | ACY<br>T | TCT<br>S | GAT<br>D | GTA<br>V |
| TCA<br>S | ATA<br>I | TAT<br>Y | CTT<br>L | GAT<br>D | GCC<br>A | ACA<br>T | TAC<br>Y | TTT<br>F | AAG<br>K | AAG<br>K | CTG<br>L |
| CAA<br>Q | CAA<br>Q | CTA<br>L | TTT<br>F | GAT<br>D | AAA<br>K | GTG<br>V | AAA<br>K | GAT<br>D | GTT<br>V | TTG<br>L | AAA<br>K |
| GAT<br>D | TCT<br>S | CCA<br>P | CAT<br>H | AAA<br>K | GAC<br>D | GAA<br>E | CCA<br>P | TTA<br>L | TGG<br>W | CTT<br>L | GGA<br>G |
| GAA<br>E | ACA<br>T | AGT<br>S | TCT<br>S | GGA<br>G | TAC<br>Y | AAC<br>N | AGC<br>S | GGC<br>G | ACA<br>T | GAA<br>E | GAT<br>D |
| GTA<br>V | TCC<br>S | GAT<br>D | CGA<br>R | TAT<br>Y | GTT<br>V | TCA<br>S | GGA<br>G | TTT<br>F | CTA<br>L | ACA<br>T | TTA<br>L |
| GAC<br>D | AAG<br>K | TTG<br>L | GGT<br>G | CTC<br>L | AGT<br>S | GCA<br>A | GCC<br>A | AAC<br>N | AAT<br>N | GTA<br>V | AAG<br>K |
| GTT<br>V | GTT<br>V | ATA<br>I | AGA<br>R | CAG<br>Q | ACA<br>T | ATA<br>I | TAC<br>Y | AAT<br>N | GGA<br>G | TAT<br>Y | TAT<br>Y |
| GGT<br>G | CTC<br>L | CTT<br>L | GAC<br>D | AAA<br>K | AAC<br>N | ACT<br>T | TTA<br>L | GAG<br>E | CCG<br>P | AAT<br>N | CCG<br>P |
| GAT<br>D | TAC<br>Y | TGG<br>W | TTA<br>L | ATG<br>M | CAT<br>H | GTT<br>V | CAT<br>H | AAT<br>N | TCT<br>S | TTG<br>L | GTC<br>V |
| GGA<br>G | AAT<br>N | ACA<br>T | GTT<br>V | TTT<br>F | AAA<br>K | GTT<br>V | GAC<br>D | GTT<br>V | AGT<br>S | GAT<br>D | CCA<br>P |
| ACT<br>T | AAT<br>N | AAA<br>K | GCA<br>A | AGA<br>R | GTT<br>V | TAC<br>Y | GCG<br>A | CAA<br>Q | TGT<br>C | ACC<br>T | AAA<br>K |
| ACA<br>T | AAT<br>N | AGC<br>S | AAA<br>K | CAT<br>H | ACT<br>T | CAA<br>Q | AGC<br>S | AGA<br>R | TAT<br>Y | TAC<br>Y | AAG<br>K |
| GGC<br>G | TCT<br>S | TTG<br>L | ACA<br>T | ATC<br>I | TTT<br>F | GCA<br>A | CTT<br>L | AAT<br>N | GTT<br>V | GGA<br>G | GAT<br>D |

Fig 8 (contnd)

| GGA | GAT | GTA | ACG | TTA | AAG | ATC | GGT | CAA | TAC | AGC | GGT |
|-----|-----|-----|-----|-----|-----|-----|-----|-----|-----|-----|-----|
| G   | D   | V   | T   | L   | K   | I   | G   | Q   | Y   | S   | G   |
| AAA | AAA | ATT | TAT | TCA | TAC | ATT | CTG | ACA | CCT | GAA | GGA |
| K   | K   | I   | Y   | S   | Y   | I   | L   | T   | P   | E   | G   |
| GGA | CAA | CTT | ACA | TCA | CAG | AAA | GTT | CTC | TTG | AAT | GGA |
| G   | Q   | L   | T   | S   | Q   | K   | V   | L   | L   | N   | G   |
| AAG | GAA | TTG | AAC | TTA | GTG | TCT | GAT | CAG | TTA | CCA | GAA |
| K   | E   | L   | N   | L   | V   | S   | D   | Q   | L   | P   | E   |
| CTA | AAT | GCA | GAT | GAA | TCC | AAA | ACA | TCT | TTC | ACC | TTA |
| L   | N   | A   | D   | E   | S   | K   | T   | S   | F   | T   | L   |
| TCC | CCA | AAG | ACA | TTT | GGT | TTT | TTT | GTT | GTT | TCC | GAT |
| S   | P   | K   | T   | F   | G   | F   | F   | V   | V   | S   | D   |
| GCT | AAT | GTT | GAA | GCA | TGY | AAR | AAR |     |     |     |     |
| A   | N   | V   | E   | A   | C   | K   | K   |     |     |     |     |

Fig. 9:

| | | | | | | | | | | | |
|---|---|---|---|---|---|---|---|---|---|---|---|
| AAA | GAG | ATT | GCC | GTG | ACA | ATT | GAC | GAT | AAG | AAT | GTG |
| K | E | I | A | V | T | I | D | D | K | N | V |
| ATT | GCA | TCT | GCC | AGT | GAG | TCT | TTC | CAT | GGA | GTT | GCC |
| I | A | S | A | S | E | S | F | H | G | V | A |
| TTT | GAT | GCG | TCT | CTA | TTT | TCG | CCC | AAG | GGT | CTT | TGG |
| F | D | A | S | L | F | S | P | K | G | L | W |
| AGC | TTT | GTT | GAT | ATT | ACC | TCT | CCA | AAA | TTG | TTC | AAA |
| S | F | V | D | I | T | S | P | K | L | F | K |
| TTG | CTG | GAA | GGA | CTT | TCT | CCT | GGA | TAC | TTC | AGG | GTT |
| L | L | E | G | L | S | P | G | Y | F | R | V |
| GGC | GGA | ACG | TTT | GCC | AAT | CGG | CTG | TTT | TTT | GAC | TTG |
| G | G | T | F | A | N | R | L | F | F | D | L |
| GAC | GAA | AAT | AAT | AAG | TGG | AAR | GAT | TAT | TGG | GCT | TTT |
| D | E | N | N | K | W | K | D | Y | W | A | F |
| AAA | GAC | AAA | ACC | CCC | GAA | ACT | GCG | ACA | ATA | ACA | AGG |
| K | D | K | T | P | E | T | A | T | I | T | R |
| AGA | TGG | CTG | TTC | AGA | AAA | CAA | AAT | AAT | CTG | AAA | AAG |
| R | W | L | F | R | K | Q | N | N | L | K | K |
| GAG | ACT | TTT | GAC | AAT | TTA | GTG | AAA | CTA | ACA | AAG | GGA |
| E | T | F | D | N | L | V | K | L | T | K | G |
| AGC | AAG | ATG | AGA | TTG | TTA | TTC | GAT | TTG | AAT | GCC | GAA |
| S | K | M | R | L | L | F | D | L | N | A | E |
| GTG | AGG | ACT | GGT | TAT | GAA | ATT | GGA | AAG | AAG | ATG | ACA |
| V | R | T | G | Y | E | I | G | K | K | M | T |
| TCC | ACT | TGG | GAT | TCA | TCG | GAG | GCT | GAA | AAG | TTA | TTT |
| S | T | W | D | S | S | E | A | E | K | L | F |
| AAA | TAT | TGT | GTG | TCA | AAA | GGT | TAC | GGA | GAC | AAT | ATC |
| K | Y | C | V | S | K | G | Y | G | D | N | I |
| GAT | TGG | GAA | CTT | GGG | AAT | GGA | CCG | GAC | CAC | ACC | TCA |
| D | W | E | L | G | N | G | P | D | H | T | S |
| GCT | CAC | AAT | TTA | ACT | GAA | AAG | CAG | GTT | GGA | GAA | GAT |
| A | H | N | L | T | E | K | Q | V | G | E | D |
| TTT | AAA | GCA | CTG | CAT | AAA | GTT | CTA | GAG | AAA | TAT | CCA |
| F | K | A | L | H | K | V | L | E | K | Y | P |
| ACT | CTT | AAC | AAG | GGA | TCG | CTC | GTT | GGT | CCA | GAT | GTA |
| T | L | N | K | G | S | L | V | G | P | D | V |

Fig 9 (contnd)

| | | | | | | | | | | | |
|---|---|---|---|---|---|---|---|---|---|---|---|
| GGG | TGG | ATG | GGC | GTC | AGT | TAC | GTC | AAG | GGA | TTG | GCA |
| G | W | M | G | V | S | Y | V | K | G | L | A |
| GAC | GAG | GCA | GGT | GAC | CAT | GTA | ACT | GCT | TTT | ACA | CTC |
| D | E | A | G | D | H | V | T | A | F | T | L |
| CAC | CAA | TAT | TAT | TTC | GAT | GGA | AAC | ACC | TCT | GAT | GTA |
| H | Q | Y | Y | F | D | G | N | T | S | D | V |
| TCA | ATA | TAT | CTT | GAT | GCC | ACA | TAC | TTT | AAG | AAG | CTG |
| S | I | Y | L | D | A | T | Y | F | K | K | L |
| CAA | CAA | CTA | TTT | GAT | AAA | GTG | AAA | GAT | GTT | TTG | AAA |
| Q | Q | L | F | D | K | V | K | D | V | L | K |
| GAT | TCT | CCA | CAT | AAA | GAC | AAA | CCA | TTA | TGG | CTT | GGA |
| D | S | P | H | K | D | K | P | L | W | L | G |
| GAA | ACA | AGT | TCT | GGA | TAC | AAC | AGC | GGC | ACA | GAA | GAT |
| E | T | S | S | G | Y | N | S | G | T | E | D |
| GTA | TCC | GAT | CGA | TAT | GTT | TCA | GGA | TTT | CTA | ACA | TTA |
| V | S | D | R | Y | V | S | G | F | L | T | L |
| GAC | AAG | TTG | GGT | CTC | AGT | GCA | GCC | AAC | AAT | GTA | AAG |
| D | K | L | G | L | S | A | A | N | N | V | K |
| GTT | GTT | ATA | AGA | CAG | ACA | ATA | TAC | AGT | GGA | TAT | TAT |
| V | V | I | R | Q | T | I | Y | S | G | Y | Y |
| GGT | CCC | CTT | GAC | AAA | AAC | ACT | TTA | GAG | CCA | AAT | CCG |
| G | P | L | D | K | N | T | L | E | P | N | P |
| GAT | TAC | TGG | TTA | ATG | CAT | GTT | CAT | AAT | TCT | TTG | GTC |
| D | Y | W | L | M | H | V | H | N | S | L | V |
| GGA | AAT | ACA | GTT | TTT | AAA | GTT | GAC | GTT | AGT | GAT | CCA |
| G | N | T | V | F | K | V | D | V | S | D | P |
| ACT | AAT | AAA | GCA | AGA | GTT | TAC | GCG | CAA | TGT | ACC | AAA |
| T | N | K | A | R | V | Y | A | Q | C | T | K |
| ACA | AAT | AGC | AAA | CAT | ACT | CAA | AGC | AGA | TAT | TAC | AAG |
| T | N | S | K | H | T | Q | S | R | Y | Y | K |
| GGC | TCT | TTG | ACA | ATC | TTT | GCA | CTT | AAT | GTT | GGA | GAT |
| G | S | L | T | I | F | A | L | N | V | G | D |
| GAA | GAT | GTA | ACG | TTA | AAG | ATC | GGT | CAA | TAC | AGC | GGT |
| E | D | V | T | L | K | I | G | Q | Y | S | G |

Fig 9 (contnd)

| AAA | AAA | ATT | TAT | TCA | TAC | ATT | CTG | ACA | CCT | GAA | GGA |
|-----|-----|-----|-----|-----|-----|-----|-----|-----|-----|-----|-----|
| K   | K   | I   | Y   | S   | Y   | I   | L   | T   | P   | E   | G   |

| GGA | CAA | CTT | ACA | TCA | CAG | AAA | GTT | CTC | TTG | AAT | GGA |
|-----|-----|-----|-----|-----|-----|-----|-----|-----|-----|-----|-----|
| G   | Q   | L   | T   | S   | Q   | K   | V   | L   | L   | N   | G   |

| AAG | GAA | TTG | AAC | TTA | RTG | TCT | GAT | CAG | TTA | CCA | CAA |
|-----|-----|-----|-----|-----|-----|-----|-----|-----|-----|-----|-----|
| K   | E   | L   | N   | L   | V   | S   | D   | Q   | L   | P   | Q   |

| CTA | AAT | GCA | YAT | GAA | TCC | AAA | ACA | TCT | TTC | ACC | TTA |
|-----|-----|-----|-----|-----|-----|-----|-----|-----|-----|-----|-----|
| L   | N   | A   | D   | E   | S   | K   | T   | S   | F   | T   | L   |

| TCC | CCA | AAG | ACA | TTT | GGT | TTT | TTT | GTT | GTT | TCC | GAT |
|-----|-----|-----|-----|-----|-----|-----|-----|-----|-----|-----|-----|
| S   | P   | K   | T   | F   | G   | F   | F   | V   | V   | S   | D   |

| GCT | AAT | GTT | GAA | GCA | TGY | AAR | AAR |
|-----|-----|-----|-----|-----|-----|-----|-----|
| A   | N   | V   | E   | A   | C   | K   | K   |

Fig. 10:

| | | | | | | | | | | | |
|---|---|---|---|---|---|---|---|---|---|---|---|
| AAA | GAG | ATT | GCC | GTG | ACA | ATT | GAC | GAT | AAG | AAT | GTG |
| K | E | I | A | V | T | I | D | D | K | N | V |
| ATT | GCA | TCT | GTC | AGT | GAG | TCT | TTC | CAT | GGA | GTT | GCC |
| I | A | S | V | S | E | S | F | H | G | V | A |
| TTT | GAT | GCG | TCT | CTA | TTC | TCG | CCC | AAG | GGT | CCT | TGG |
| F | D | A | S | L | F | S | P | K | G | P | W |
| AGC | TTT | GTT | AAT | ATT | ACC | TCT | CCA | AAA | TTG | TTC | AAA |
| S | F | V | N | I | T | S | P | K | L | F | K |
| TTG | CTG | GAA | GGA | CTT | TCT | CCT | GGA | TAC | TTC | AGG | GTT |
| L | L | E | G | L | S | P | G | Y | F | R | V |
| GGC | GGA | ACG | TTT | GCC | AAT | TGG | CTG | TTT | TTT | GAC | TTG |
| G | G | T | F | A | N | W | L | F | F | D | L |
| GAC | GAA | AAT | AAT | AAG | TGG | AAG | GAT | TAT | TGG | GCT | TTT |
| D | E | N | N | K | W | K | D | Y | W | A | F |
| AAA | GAC | AAA | ACC | CCC | GAA | ACT | GCG | ACA | ATA | ACA | AGG |
| K | D | K | T | P | E | T | A | T | I | T | R |
| AGA | TGG | CTG | TTC | AGA | AAA | CAA | AAT | AAT | CTG | AAA | AAG |
| R | W | L | F | R | K | Q | N | N | L | K | K |
| GAG | ACT | TTT | GAC | GAT | TTA | GTG | AAA | CTA | ACA | AAG | GGA |
| E | T | F | D | D | L | V | K | L | T | K | G |
| AGC | AAG | ATG | AGA | TTG | TTA | TTC | GAT | TTG | AAT | GCC | GAA |
| S | K | M | R | L | L | F | D | L | N | A | E |
| GTG | AGG | ACT | GGT | TAT | GAA | ATT | GGA | AAG | AAG | ACG | ACA |
| V | R | T | G | Y | E | I | G | K | K | T | T |
| TCC | ACT | TGG | GAT | TCA | TCG | GAG | GCT | GAA | AAG | TTA | TTT |
| S | T | W | D | S | S | E | A | E | K | L | F |
| AAA | TAT | TGT | GTG | TCA | AAA | GGT | TAC | GGA | GAC | AAT | ATC |
| K | Y | C | V | S | K | G | Y | G | D | N | I |
| GAT | TGG | GAA | CTT | GGA | AAT | GAA | CCG | GAC | CAC | ACC | TCA |
| D | W | E | L | G | N | E | P | D | H | T | S |
| GCT | CAC | AAT | TTA | ACT | GAA | AAG | CAG | GTT | GGA | GAA | GAT |
| A | H | N | L | T | E | K | Q | V | G | E | D |
| TTC | AAA | GCA | CTG | CAT | AAA | GTT | TTA | GAG | AAA | TAT | CCA |
| F | K | A | L | H | K | V | L | E | K | Y | P |

Fig 10 (contnd)

| | | | | | | | | | | | |
|---|---|---|---|---|---|---|---|---|---|---|---|
| ACT | CTT | AAC | AAG | GGA | TCG | CCC | GTT | GGT | CCA | GAT | GTA |
| T | L | N | K | G | S | P | V | G | P | D | V |
| GGG | TGG | ATG | GGC | GTC | AGC | TAC | GTC | AAG | GGA | TTG | GCA |
| G | W | M | G | V | S | Y | V | K | G | L | A |
| GAC | GGG | GCA | GGT | GAC | CTT | GTA | ACT | GCT | TTT | ACA | CTA |
| D | G | A | G | D | L | V | T | A | F | T | L |
| CAC | CAA | TAT | TAT | TTC | GAT | GGA | AAC | ACC | TCT | GAT | GTA |
| H | Q | Y | Y | F | D | G | N | T | S | D | V |
| TCA | ACA | TAT | CTT | GAT | GCC | TCA | TAC | TTT | AAA | AAG | CTG |
| S | T | Y | L | D | A | S | Y | F | K | K | L |
| CAA | CAG | CTG | TTT | GAT | AAA | GTG | AAA | GAT | GTT | TTG | AAA |
| Q | Q | L | F | D | K | V | K | D | V | L | K |
| AAT | TCT | CCA | CAT | AAA | GAC | AAA | CCA | TTA | TGG | CTT | GGA |
| N | S | P | H | K | D | K | P | L | W | L | G |
| GAG | ACA | AGT | TCT | GGA | TGC | AAC | AGC | GGC | ACA | AAA | GAT |
| E | T | S | S | G | Y | N | S | G | T | K | D |
| GTA | TCC | GAT | CGA | TAT | GTT | TCA | GGA | TTT | CTA | ACA | TTA |
| V | S | D | R | Y | V | S | G | F | L | T | L |
| GAC | AAG | TTG | GGT | CTC | AGT | GCA | GCC | AAC | AAT | GTA | AAG |
| D | K | L | G | L | S | A | A | N | N | V | K |
| GTT | GTT | ATA | AGA | CAG | ACA | ATA | TAC | AAT | GGA | TAT | TAT |
| V | V | I | R | Q | T | I | Y | N | G | Y | Y |
| GGT | CTC | CTT | GAT | AAA | AAC | ACT | TTA | GAG | CCA | AAT | CCT |
| G | L | L | D | K | N | T | L | E | P | N | P |
| GAT | TAC | TGG | TTA | ATG | CAT | GTT | CAC | AAT | TCT | TTG | GTC |
| D | Y | W | L | M | H | V | H | N | S | L | V |
| GGA | AAT | ACA | GTT | TTT | AAA | GTT | GAC | GTT | GGT | GAT | CCA |
| G | N | T | V | F | K | V | D | V | G | D | P |
| ACT | AAT | AAA | ACG | AGA | GTC | TAT | GCA | CAA | TGT | ACC | AAG |
| T | N | K | T | R | V | Y | A | Q | C | T | K |
| ACA | AAT | AGC | AAA | CAC | ACT | CAA | GGC | AAG | TAT | TAC | AAG |
| T | N | S | K | H | T | Q | G | K | Y | Y | K |
| GGC | TCT | TTG | ACA | ATC | TTT | GCA | CTT | AAT | GTT | GGA | GAT |
| G | S | L | T | I | F | A | L | N | V | G | D |

Fig 10 (contnd)

| GAA | GAA | GTA | ACG | TTA | AAG | ATC | GAT | CAA | TAC | GGC | GGT |
|-----|-----|-----|-----|-----|-----|-----|-----|-----|-----|-----|-----|
| E   | E   | V   | T   | L   | K   | I   | D   | Q   | Y   | G   | G   |

| AAA | AAA | ATT | TAT | TCA | TAC | ATT | CTG | ACA | CCT | GAA | GGA |
|-----|-----|-----|-----|-----|-----|-----|-----|-----|-----|-----|-----|
| K   | K   | I   | Y   | S   | Y   | I   | L   | T   | P   | E   | G   |

| GGA | CAA | CTT | ACA | TCA | CAG | AAA | GTT | CTC | TTG | AAT | GGA |
|-----|-----|-----|-----|-----|-----|-----|-----|-----|-----|-----|-----|
| G   | Q   | L   | T   | S   | Q   | K   | V   | L   | L   | N   | G   |

| AAG | GAA | TTG | AAC | TTA | GTG | TCT | GAT | CAG | TTA | CCA | GAA |
|-----|-----|-----|-----|-----|-----|-----|-----|-----|-----|-----|-----|
| K   | E   | L   | N   | L   | V   | S   | D   | Q   | L   | P   | E   |

| CTA | AAT | GCA | GAT | GAA | TCC | AAA | ACA | TCT | TTC | ACC | TTA |
|-----|-----|-----|-----|-----|-----|-----|-----|-----|-----|-----|-----|
| L   | N   | A   | D   | E   | S   | K   | T   | S   | F   | T   | L   |

| TCC | CCA | AAG | ACA | TTT | GGT | TTT | TTT | GTT | GTT | TCC | GAT |
|-----|-----|-----|-----|-----|-----|-----|-----|-----|-----|-----|-----|
| S   | P   | K   | T   | F   | G   | F   | F   | V   | V   | S   | D   |

| GCT | AAT | GTT | GAA | GCA | TGY | AAR | AAR |
|-----|-----|-----|-----|-----|-----|-----|-----|
| A   | N   | V   | E   | A   | C   | K   | K   |

SEQUENCE LISTING

```
<160> NUMBER OF SEQ ID NOS: 20

<210> SEQ ID NO 1
<211> LENGTH: 488
<212> TYPE: PRT
<213> ORGANISM: Hirudinaria manillensis

<400> SEQUENCE: 1

Lys Glu Ile Ala Val Thr Ile Asp Asp Lys Asn Val Ile Ala Ser Val
  1               5                  10                  15

Ser Glu Ser Phe His Gly Val Ala Phe Asp Ala Ser Leu Phe Ser Pro
             20                  25                  30

Lys Gly Leu Trp Ser Phe Val Asp Ile Thr Ser Pro Lys Leu Phe Lys
         35                  40                  45

Leu Leu Glu Gly Leu Ser Pro Gly Tyr Phe Arg Val Gly Gly Thr Phe
     50                  55                  60

Ala Asn Trp Leu Phe Phe Asp Leu Asp Glu Asn Asn Lys Trp Lys Asp
 65                  70                  75                  80

Tyr Trp Ala Phe Lys Asp Lys Thr Pro Glu Thr Ala Thr Ile Thr Arg
                 85                  90                  95

Arg Trp Leu Phe Arg Lys Gln Asn Asn Leu Lys Lys Glu Thr Glu Asp
            100                 105                 110

Asp Leu Val Lys Leu Thr Lys Gly Ser Lys Met Arg Leu Leu Phe Asp
        115                 120                 125

Leu Asn Ala Glu Val Arg Thr Gly Tyr Glu Ile Gly Lys Lys Met Thr
    130                 135                 140

Ser Thr Trp Asp Ser Ser Glu Ala Glu Lys Leu Phe Lys Tyr Cys Val
145                 150                 155                 160

Ser Lys Gly Tyr Gly Asp Asn Ile Asp Trp Glu Leu Gly Asn Glu Pro
                165                 170                 175

Asp His Thr Ser Ala His Asn Leu Thr Glu Lys Gln Val Gly Glu Asp
            180                 185                 190

Phe Lys Ala Leu His Lys Val Leu Glu Lys Tyr Pro Thr Leu Asn Lys
        195                 200                 205

Gly Ser Leu Val Gly Pro Asp Val Gly Trp Met Gly Val Ser Tyr Val
    210                 215                 220

Lys Gly Leu Ala Asp Gly Ala Gly Asp Leu Val Thr Ala Phe Thr Leu
225                 230                 235                 240
```

```
His Gln Tyr Tyr Phe Asp Gly Asn Thr Ser Asp Val Ser Thr Tyr Leu
                245                 250                 255

Asp Ala Thr Tyr Phe Lys Lys Leu Gln Gln Leu Phe Asp Lys Val Lys
                260                 265                 270

Asp Val Leu Lys Asn Ser Gln His Lys Asp Lys Pro Leu Trp Leu Gly
            275                 280                 285

Glu Thr Ser Ser Gly Tyr Asn Ser Gly Thr Lys Asp Val Ser Asp Arg
290                 295                 300

Tyr Val Ser Gly Phe Leu Thr Leu Asp Lys Leu Gly Leu Ser Ala Ala
305                 310                 315                 320

Asn Asn Val Lys Val Ile Arg Gln Thr Ile Tyr Asn Gly Tyr Tyr
                325                 330                 335

Gly Leu Leu Asp Lys Asn Thr Leu Glu Pro Asn Pro Asp Tyr Trp Leu
                340                 345                 350

Met His Val His Asn Ser Leu Val Gly Asn Thr Val Phe Lys Val Asp
            355                 360                 365

Val Ser Asp Pro Thr Asn Lys Ala Arg Val Tyr Ala Gln Cys Thr Lys
            370                 375                 380

Thr Asn Ser Lys His Thr Gln Ser Arg Tyr Tyr Lys Gly Ser Leu Thr
385                 390                 395                 400

Ile Phe Ala Leu Asn Val Gly Asp Glu Asp Val Thr Leu Lys Ile Asp
                405                 410                 415

Gln Tyr Gly Gly Lys Lys Ile Tyr Ser Tyr Ile Leu Thr Pro Glu Gly
            420                 425                 430

Gly Gln Leu Thr Ser Gln Lys Val Leu Leu Asn Gly Lys Glu Leu Lys
            435                 440                 445

Leu Val Ser Asp Gln Leu Pro Glu Leu Asn Ala Asn Glu Ser Lys Thr
            450                 455                 460

Ser Phe Thr Leu Ser Pro Lys Thr Phe Gly Phe Phe Val Val Ser Asp
465                 470                 475                 480

Ala Asn Val Glu Ala Cys Lys Lys
                485

<210> SEQ ID NO 2
<211> LENGTH: 1464
<212> TYPE: DNA
<213> ORGANISM: Hirudinaria manillensis
<220> FEATURE:
<221> NAME/KEY: CDS
<222> LOCATION: (1)..(1464)
<220> FEATURE:
<221> NAME/KEY: variation
<222> LOCATION: (667)..(669)
<223> OTHER INFORMATION: This codon codes for a Tyr or Asn

<400> SEQUENCE: 2 aaa gag att gcc gtg aca att gac gat aag aat gtg att gca tct gcc    48
Lys Glu Ile Ala Val Thr Ile Asp Asp Lys Asn Val Ile Ala Ser Ala
 1               5                  10                  15 agt ggg tct ttc ctt gga gtt gcc ttt gat gcg tct cta ttt tcg ccc    96
Ser Gly Ser Phe Leu Gly Val Ala Phe Asp Ala Ser Leu Phe Ser Pro
             20                  25                  30 aag ggt ctt tgg agc ttt gtt gat att acc tct cca aaa ttg ttc aaa   144
Lys Gly Leu Trp Ser Phe Val Asp Ile Thr Ser Pro Lys Leu Phe Lys
         35                  40                  45 ttg ctg gaa gga ctt tct cct gga tac ttc agg gtt ggc gga acg ttt   192
Leu Leu Glu Gly Leu Ser Pro Gly Tyr Phe Arg Val Gly Gly Thr Phe
     50                  55                  60
```

-continued

| | | |
|---|---|---|
| gcc aat tgg ctg ttt ttt gac ttg gac gaa aat aat aag tgg aag gat<br>Ala Asn Trp Leu Phe Phe Asp Leu Asp Glu Asn Asn Lys Trp Lys Asp<br>65                        70                          75                        80 | 240 |
| tat tgg gct ttt aaa gac aaa acc ccc gaa act gca aca ata aca agg<br>Tyr Trp Ala Phe Lys Asp Lys Thr Pro Glu Thr Ala Thr Ile Thr Arg<br>85                        90                        95 | 288 |
| aga tgg ctg ttc aga aaa caa aat aat ctg aaa aag gag act ttt gac<br>Arg Trp Leu Phe Arg Lys Gln Asn Asn Leu Lys Lys Glu Thr Phe Asp<br>100                      105                      110 | 336 |
| aat tta gtg aaa cta aca aag gga agc aag atg aga ttg tta ttc gat<br>Asn Leu Val Lys Leu Thr Lys Gly Ser Lys Met Arg Leu Leu Phe Asp<br>115                      120                      125 | 384 |
| ttg aat gcc gaa gtg agg act ggt tat gaa att gga aag aag atg aca<br>Leu Asn Ala Glu Val Arg Thr Gly Tyr Glu Ile Gly Lys Lys Met Thr<br>130                      135                      140 | 432 |
| tcc act tgg gat tca tcg gag gct gaa aag tta ttt aaa tat tgt gtg<br>Ser Thr Trp Asp Ser Ser Glu Ala Glu Lys Leu Phe Lys Tyr Cys Val<br>145                      150                      155                      160 | 480 |
| tca aaa ggt tac gga gac aat atc gat tgg gaa ctt gga aat gaa ccg<br>Ser Lys Gly Tyr Gly Asp Asn Ile Asp Trp Glu Leu Gly Asn Glu Pro<br>                            165                      170                      175 | 528 |
| gac cac acc tca gct cac aat tta act gaa aag cag gtt gga gaa gat<br>Asp His Thr Ser Ala His Asn Leu Thr Glu Lys Gln Val Gly Glu Asp<br>                  180                      185                      190 | 576 |
| ttt aaa gca ctg cat aaa gtt cta gag aaa tat cca act ctt aac aag<br>Phe Lys Ala Leu His Lys Val Leu Glu Lys Tyr Pro Thr Leu Asn Lys<br>                  195                      200                      205 | 624 |
| gga tcg ctc gtt ggt cca gat gta ggg tgg atg ggc gtc agt wac gtc<br>Gly Ser Leu Val Gly Pro Asp Val Gly Trp Met Gly Val Ser Xaa Val<br>210                      215                      220 | 672 |
| aag gga ttg gca gac gag gcr ggt gac cat gta ack gct ttt aca ctc<br>Lys Gly Leu Ala Asp Glu Ala Gly Asp His Val Thr Ala Phe Thr Leu<br>225                      230                      235                      240 | 720 |
| cac caa tat tat ttc gat gga aac acy tct gat gta tca ata tat ctt<br>His Gln Tyr Tyr Phe Asp Gly Asn Thr Ser Asp Val Ser Ile Tyr Leu<br>                  245                      250                      255 | 768 |
| gat gcc aca tac ttt aag aag ctg caa caa cta ttt gat aaa gtg aaa<br>Asp Ala Thr Tyr Phe Lys Lys Leu Gln Gln Leu Phe Asp Lys Val Lys<br>260                      265                      270 | 816 |
| gat gtt ttg aaa gat tct cca cat aaa gac gaa cca tta tgg ctt gga<br>Asp Val Leu Lys Asp Ser Pro His Lys Asp Glu Pro Leu Trp Leu Gly<br>                  275                      280                      285 | 864 |
| gaa aca agt tct gga tac aac agc ggc aca gaa gat gta tcc gat cga<br>Glu Thr Ser Ser Gly Tyr Asn Ser Gly Thr Glu Asp Val Ser Asp Arg<br>290                      295                      300 | 912 |
| tat gtt tca gga ttt cta aca tta gac aag ttg ggt ctc agt gca gcc<br>Tyr Val Ser Gly Phe Leu Thr Leu Asp Lys Leu Gly Leu Ser Ala Ala<br>305                      310                      315                      320 | 960 |
| aac aat gta aag gtt gtt ata aga cag aca ata tac aat gga tat tat<br>Asn Asn Val Lys Val Val Ile Arg Gln Thr Ile Tyr Asn Gly Tyr Tyr<br>                  325                      330                      335 | 1008 |
| ggt ctc ctt gac aaa aac act tta gag ccg aat ccg gat tac tgg tta<br>Gly Leu Leu Asp Lys Asn Thr Leu Glu Pro Asn Pro Asp Tyr Trp Leu<br>340                      345                      350 | 1056 |
| atg cat gtt cat aat tct ttg gtc gga aat aca gtt ttt aaa gtt gac<br>Met His Val His Asn Ser Leu Val Gly Asn Thr Val Phe Lys Val Asp<br>                  355                      360                      365 | 1104 |
| gtt agt gat cca act aat aaa gca aga gtt tac gcg caa tgt acc aaa<br>Val Ser Asp Pro Thr Asn Lys Ala Arg Val Tyr Ala Gln Cys Thr Lys<br>370                      375                      380 | 1152 |

```
aca aat agc aaa cat act caa agc aga tat tac aag ggc tct ttg aca    1200
Thr Asn Ser Lys His Thr Gln Ser Arg Tyr Tyr Lys Gly Ser Leu Thr
385                 390                 395                 400 atc ttt gca ctt aat gtt gga gat gga gat gta acg tta aag atc ggt    1248
Ile Phe Ala Leu Asn Val Gly Asp Gly Asp Val Thr Leu Lys Ile Gly
                405                 410                 415 caa tac agc ggt aaa aaa att tat tca tac att ctg aca cct gaa gga    1296
Gln Tyr Ser Gly Lys Lys Ile Tyr Ser Tyr Ile Leu Thr Pro Glu Gly
            420                 425                 430 gga caa ctt aca tca cag aaa gtt ctc ttg aat gga aag gaa ttg aac    1344
Gly Gln Leu Thr Ser Gln Lys Val Leu Leu Asn Gly Lys Glu Leu Asn
        435                 440                 445 tta gtg tct gat cag tta cca gaa cta aat gca gat gaa tcc aaa aca    1392
Leu Val Ser Asp Gln Leu Pro Glu Leu Asn Ala Asp Glu Ser Lys Thr
450                 455                 460 tct ttc acc tta tcc cca aag aca ttt ggt ttt ttt gtt gtt tcc gat    1440
Ser Phe Thr Leu Ser Pro Lys Thr Phe Gly Phe Phe Val Val Ser Asp
465                 470                 475                 480 gct aat gtt gaa gca tgy aar aar                                    1464
Ala Asn Val Glu Ala Cys Lys Lys
                485
```

<210> SEQ ID NO 3
<211> LENGTH: 488
<212> TYPE: PRT
<213> ORGANISM: Hirudinaria manillensis
<220> FEATURE:
<221> NAME/KEY: variation
<222> LOCATION: (223)
<223> OTHER INFORMATION: Tyr or Asn

<400> SEQUENCE: 3

```
Lys Glu Ile Ala Val Thr Ile Asp Asp Lys Asn Val Ile Ala Ser Ala
  1               5                  10                  15

Ser Gly Ser Phe Leu Gly Val Ala Phe Asp Ala Ser Leu Phe Ser Pro
            20                  25                  30

Lys Gly Leu Trp Ser Phe Val Asp Ile Thr Ser Pro Lys Leu Phe Lys
        35                  40                  45

Leu Leu Glu Gly Leu Ser Pro Gly Tyr Phe Arg Val Gly Gly Thr Phe
    50                  55                  60

Ala Asn Trp Leu Phe Phe Asp Leu Asp Glu Asn Asn Lys Trp Lys Asp
 65                  70                  75                  80

Tyr Trp Ala Phe Lys Asp Lys Thr Pro Glu Thr Ala Thr Ile Thr Arg
                85                  90                  95

Arg Trp Leu Phe Arg Lys Gln Asn Asn Leu Lys Lys Glu Thr Phe Asp
            100                 105                 110

Asn Leu Val Lys Leu Thr Lys Gly Ser Lys Met Arg Leu Leu Phe Asp
        115                 120                 125

Leu Asn Ala Glu Val Arg Thr Gly Tyr Glu Ile Gly Lys Lys Met Thr
    130                 135                 140

Ser Thr Trp Asp Ser Ser Glu Ala Glu Lys Leu Phe Lys Tyr Cys Val
145                 150                 155                 160

Ser Lys Gly Tyr Gly Asp Asn Ile Asp Trp Glu Leu Gly Asn Glu Pro
                165                 170                 175

Asp His Thr Ser Ala His Asn Leu Thr Glu Lys Gln Val Gly Glu Asp
            180                 185                 190

Phe Lys Ala Leu His Lys Val Leu Glu Lys Tyr Pro Thr Leu Asn Lys
        195                 200                 205
```

```
Gly Ser Leu Val Gly Pro Asp Val Gly Trp Met Gly Val Ser Xaa Val
        210                 215                 220
Lys Gly Leu Ala Asp Glu Ala Gly Asp His Val Thr Ala Phe Thr Leu
225                 230                 235                 240
His Gln Tyr Tyr Phe Asp Gly Asn Thr Ser Asp Val Ser Ile Tyr Leu
                    245                 250                 255
Asp Ala Thr Tyr Phe Lys Lys Leu Gln Gln Leu Phe Asp Lys Val Lys
                260                 265                 270
Asp Val Leu Lys Asp Ser Pro His Lys Asp Glu Pro Leu Trp Leu Gly
            275                 280                 285
Glu Thr Ser Ser Gly Tyr Asn Ser Gly Thr Glu Asp Val Ser Asp Arg
        290                 295                 300
Tyr Val Ser Gly Phe Leu Thr Leu Asp Lys Leu Gly Leu Ser Ala Ala
305                 310                 315                 320
Asn Asn Val Lys Val Ile Arg Gln Thr Ile Tyr Asn Gly Tyr Tyr
                    325                 330                 335
Gly Leu Leu Asp Lys Asn Thr Leu Glu Pro Asn Pro Asp Tyr Trp Leu
                340                 345                 350
Met His Val His Asn Ser Leu Val Gly Asn Thr Val Phe Lys Val Asp
            355                 360                 365
Val Ser Asp Pro Thr Asn Lys Ala Arg Val Tyr Ala Gln Cys Thr Lys
        370                 375                 380
Thr Asn Ser Lys His Thr Gln Ser Arg Tyr Tyr Lys Gly Ser Leu Thr
385                 390                 395                 400
Ile Phe Ala Leu Asn Val Gly Asp Gly Asp Val Thr Leu Lys Ile Gly
                    405                 410                 415
Gln Tyr Ser Gly Lys Lys Ile Tyr Ser Tyr Ile Leu Thr Pro Glu Gly
                420                 425                 430
Gly Gln Leu Thr Ser Gln Lys Val Leu Leu Asn Gly Lys Glu Leu Asn
            435                 440                 445
Leu Val Ser Asp Gln Leu Pro Glu Leu Asn Ala Asp Glu Ser Lys Thr
        450                 455                 460
Ser Phe Thr Leu Ser Pro Lys Thr Phe Gly Phe Val Val Ser Asp
465                 470                 475                 480
Ala Asn Val Glu Ala Cys Lys Lys
                485

<210> SEQ ID NO 4
<211> LENGTH: 1464
<212> TYPE: DNA
<213> ORGANISM: Hirudinaria manillensis
<220> FEATURE:
<221> NAME/KEY: CDS
<222> LOCATION: (1)..(1464)

<400> SEQUENCE: 4 aaa gag att gcc gtg aca att gac gat aag aat gtg att gca tct gcc    48
Lys Glu Ile Ala Val Thr Ile Asp Asp Lys Asn Val Ile Ala Ser Ala
1               5                   10                  15 agt gag tct ttc cat gga gtt gcc ttt gat gcg tct cta ttt tcg ccc    96
Ser Glu Ser Phe His Gly Val Ala Phe Asp Ala Ser Leu Phe Ser Pro
            20                  25                  30 aag ggt ctt tgg agc ttt gtt gat att acc tct cca aaa ttg ttc aaa   144
Lys Gly Leu Trp Ser Phe Val Asp Ile Thr Ser Pro Lys Leu Phe Lys
        35                  40                  45 ttg ctg gaa gga ctt tct cct gga tac ttc agg gtt ggc gga acg ttt   192
```

-continued

| | | |
|---|---|---|
| Leu Leu Glu Gly Leu Ser Pro Gly Tyr Phe Arg Val Gly Gly Thr Phe<br>     50                      55                      60 | | |
| gcc aat cgg ctg ttt ttt gac ttg gac gaa aat aat aag tgg aar gat<br>Ala Asn Arg Leu Phe Phe Asp Leu Asp Glu Asn Asn Lys Trp Lys Asp<br> 65                    70                     75                  80 | 240 |
| tat tgg gct ttt aaa gac aaa acc ccc gaa act gcg aca ata aca agg<br>Tyr Trp Ala Phe Lys Asp Lys Thr Pro Glu Thr Ala Thr Ile Thr Arg<br>                  85                   90                  95 | 288 |
| aga tgg ctg ttc aga aaa caa aat aat ctg aaa aag gag act ttt gac<br>Arg Trp Leu Phe Arg Lys Gln Asn Asn Leu Lys Lys Glu Thr Phe Asp<br>                 100               105               110 | 336 |
| aat tta gtg aaa cta aca aag gga agc aag atg aga ttg tta ttc gat<br>Asn Leu Val Lys Leu Thr Lys Gly Ser Lys Met Arg Leu Leu Phe Asp<br>        115                   120               125 | 384 |
| ttg aat gcc gaa gtg agg act ggt tat gaa att gga aag aag atg aca<br>Leu Asn Ala Glu Val Arg Thr Gly Tyr Glu Ile Gly Lys Lys Met Thr<br>     130                     135               140 | 432 |
| tcc act tgg gat tca tcg gag gct gaa aag tta ttt aaa tat tgt gtg<br>Ser Thr Trp Asp Ser Ser Glu Ala Glu Lys Leu Phe Lys Tyr Cys Val<br>145                    150               155               160 | 480 |
| tca aaa ggt tac gga gac aat atc gat tgg gaa ctt ggg aat gga ccg<br>Ser Lys Gly Tyr Gly Asp Asn Ile Asp Trp Glu Leu Gly Asn Gly Pro<br>               165               170               175 | 528 |
| gac cac acc tca gct cac aat tta act gaa aag cag gtt gga gaa gat<br>Asp His Thr Ser Ala His Asn Leu Thr Glu Lys Gln Val Gly Glu Asp<br>        180                   185               190 | 576 |
| ttt aaa gca ctg cat aaa gtt cta gag aaa tat cca act ctt aac aag<br>Phe Lys Ala Leu His Lys Val Leu Glu Lys Tyr Pro Thr Leu Asn Lys<br>     195                     200               205 | 624 |
| gga tcg ctc gtt ggt cca gat gta ggg tgg atg ggc gtc agt tac gtc<br>Gly Ser Leu Val Gly Pro Asp Val Gly Trp Met Gly Val Ser Tyr Val<br>210                    215               220 | 672 |
| aag gga ttg gca gac gag gca ggt gac cat gta act gct ttt aca ctc<br>Lys Gly Leu Ala Asp Glu Ala Gly Asp His Val Thr Ala Phe Thr Leu<br>225                    230               235              240 | 720 |
| cac caa tat tat ttc gat gga aac acc tct gat gta tca ata tat ctt<br>His Gln Tyr Tyr Phe Asp Gly Asn Thr Ser Asp Val Ser Ile Tyr Leu<br>               245               250               255 | 768 |
| gat gcc aca tac ttt aag aag ctg caa caa cta ttt gat aaa gtg aaa<br>Asp Ala Thr Tyr Phe Lys Lys Leu Gln Gln Leu Phe Asp Lys Val Lys<br>        260                   265               270 | 816 |
| gat gtt ttg aaa gat tct cca cat aaa gac aaa cca tta tgg ctt gga<br>Asp Val Leu Lys Asp Ser Pro His Lys Asp Lys Pro Leu Trp Leu Gly<br>     275                     280               285 | 864 |
| gaa aca agt tct gga tac aac agc ggc aca gaa gat gta tcc gat cga<br>Glu Thr Ser Ser Gly Tyr Asn Ser Gly Thr Glu Asp Val Ser Asp Arg<br>290                    295               300 | 912 |
| tat gtt tca gga ttt cta aca tta gac aag ttg ggt ctc agt gca gcc<br>Tyr Val Ser Gly Phe Leu Thr Leu Asp Lys Leu Gly Leu Ser Ala Ala<br>305                    310               315              320 | 960 |
| aac aat gta aag gtt gtt ata aga cag aca ata tac agt gga tat tat<br>Asn Asn Val Lys Val Val Ile Arg Gln Thr Ile Tyr Ser Gly Tyr Tyr<br>               325               330               335 | 1008 |
| ggt ccc ctt gac aaa aac act tta gag cca aat ccg gat tac tgg tta<br>Gly Pro Leu Asp Lys Asn Thr Leu Glu Pro Asn Pro Asp Tyr Trp Leu<br>        340                   345               350 | 1056 |
| atg cat gtt cat aat tct ttg gtc gga aat aca gtt ttt aaa gtt gac<br>Met His Val His Asn Ser Leu Val Gly Asn Thr Val Phe Lys Val Asp<br>     355                     360               365 | 1104 |

```
gtt agt gat cca act aat aaa gca aga gtt tac gcg caa tgt acc aaa     1152
Val Ser Asp Pro Thr Asn Lys Ala Arg Val Tyr Ala Gln Cys Thr Lys
    370                 375                 380 aca aat agc aaa cat act caa agc aga tat tac aag ggc tct ttg aca     1200
Thr Asn Ser Lys His Thr Gln Ser Arg Tyr Tyr Lys Gly Ser Leu Thr
385                 390                 395                 400 atc ttt gca ctt aat gtt gga gat gaa gat gta acg tta aag atc ggt     1248
Ile Phe Ala Leu Asn Val Gly Asp Glu Asp Val Thr Leu Lys Ile Gly
                405                 410                 415 caa tac agc ggt aaa aaa att tat tca tac att ctg aca cct gaa gga     1296
Gln Tyr Ser Gly Lys Lys Ile Tyr Ser Tyr Ile Leu Thr Pro Glu Gly
            420                 425                 430 gga caa ctt aca tca cag aaa gtt ctc ttg aat gga aag gaa ttg aac     1344
Gly Gln Leu Thr Ser Gln Lys Val Leu Leu Asn Gly Lys Glu Leu Asn
        435                 440                 445 tta rtg tct gat cag tta cca caa cta aat gca gat gaa tcc aaa aca     1392
Leu Val Ser Asp Gln Leu Pro Gln Leu Asn Ala Asp Glu Ser Lys Thr
450                 455                 460 tct ttc acc tta tcc cca aag aca ttt ggt ttt ttt gtt gtt tcc gat     1440
Ser Phe Thr Leu Ser Pro Lys Thr Phe Gly Phe Phe Val Val Ser Asp
465                 470                 475                 480 gct aat gtt gaa gca tgy aar aar                                     1464
Ala Asn Val Glu Ala Cys Lys Lys
                485

<210> SEQ ID NO 5
<211> LENGTH: 488
<212> TYPE: PRT
<213> ORGANISM: Hirudinaria manillensis

<400> SEQUENCE: 5

Lys Glu Ile Ala Val Thr Ile Asp Asp Lys Asn Val Ile Ala Ser Ala
1               5                   10                  15

Ser Glu Ser Phe His Gly Val Ala Phe Asp Ala Ser Leu Phe Ser Pro
            20                  25                  30

Lys Gly Leu Trp Ser Phe Val Asp Ile Thr Ser Pro Lys Leu Phe Lys
        35                  40                  45

Leu Leu Glu Gly Leu Ser Pro Gly Tyr Phe Arg Val Gly Gly Thr Phe
    50                  55                  60

Ala Asn Arg Leu Phe Phe Asp Leu Asp Glu Asn Asn Lys Trp Lys Asp
65                  70                  75                  80

Tyr Trp Ala Phe Lys Asp Lys Thr Pro Glu Thr Ala Thr Ile Thr Arg
                85                  90                  95

Arg Trp Leu Phe Arg Lys Gln Asn Asn Leu Lys Lys Glu Thr Phe Asp
            100                 105                 110

Asn Leu Val Lys Leu Thr Lys Gly Ser Lys Met Arg Leu Leu Phe Asp
        115                 120                 125

Leu Asn Ala Glu Val Arg Thr Gly Tyr Glu Ile Gly Lys Lys Met Thr
    130                 135                 140

Ser Thr Trp Asp Ser Ser Glu Ala Glu Lys Leu Phe Lys Tyr Cys Val
145                 150                 155                 160

Ser Lys Gly Tyr Gly Asp Asn Ile Asp Trp Glu Leu Gly Asn Gly Pro
                165                 170                 175

Asp His Thr Ser Ala His Asn Leu Thr Glu Lys Gln Val Gly Glu Asp
            180                 185                 190

Phe Lys Ala Leu His Lys Val Leu Glu Lys Tyr Pro Thr Leu Asn Lys
        195                 200                 205
```

```
Gly Ser Leu Val Gly Pro Asp Val Gly Trp Met Gly Val Ser Tyr Val
    210                 215                 220
Lys Gly Leu Ala Asp Glu Ala Gly Asp His Val Thr Ala Phe Thr Leu
225                 230                 235                 240
His Gln Tyr Tyr Phe Asp Gly Asn Thr Ser Asp Val Ser Ile Tyr Leu
                245                 250                 255
Asp Ala Thr Tyr Phe Lys Lys Leu Gln Gln Leu Phe Asp Lys Val Lys
            260                 265                 270
Asp Val Leu Lys Asp Ser Pro His Lys Asp Lys Pro Leu Trp Leu Gly
        275                 280                 285
Glu Thr Ser Ser Gly Tyr Asn Ser Gly Thr Glu Asp Val Ser Asp Arg
    290                 295                 300
Tyr Val Ser Gly Phe Leu Thr Leu Asp Lys Leu Gly Leu Ser Ala Ala
305                 310                 315                 320
Asn Asn Val Lys Val Val Ile Arg Gln Thr Ile Tyr Ser Gly Tyr Tyr
                325                 330                 335
Gly Pro Leu Asp Lys Asn Thr Leu Glu Pro Asn Pro Asp Tyr Trp Leu
            340                 345                 350
Met His Val His Asn Ser Leu Val Gly Asn Thr Val Phe Lys Val Asp
        355                 360                 365
Val Ser Asp Pro Thr Asn Lys Ala Arg Val Tyr Ala Gln Cys Thr Lys
    370                 375                 380
Thr Asn Ser Lys His Thr Gln Ser Arg Tyr Tyr Lys Gly Ser Leu Thr
385                 390                 395                 400
Ile Phe Ala Leu Asn Val Gly Asp Glu Asp Val Thr Leu Lys Ile Gly
                405                 410                 415
Gln Tyr Ser Gly Lys Lys Ile Tyr Ser Tyr Ile Leu Thr Pro Glu Gly
            420                 425                 430
Gly Gln Leu Thr Ser Gln Lys Val Leu Leu Asn Gly Lys Glu Leu Asn
        435                 440                 445
Leu Val Ser Asp Gln Leu Pro Gln Leu Asn Ala Asp Glu Ser Lys Thr
    450                 455                 460
Ser Phe Thr Leu Ser Pro Lys Thr Phe Gly Phe Val Val Ser Asp
465                 470                 475                 480
Ala Asn Val Glu Ala Cys Lys Lys
                485
```

<210> SEQ ID NO 6
<211> LENGTH: 1464
<212> TYPE: DNA
<213> ORGANISM: Hirudinaria manillensis
<220> FEATURE:
<221> NAME/KEY: CDS
<222> LOCATION: (1)..(1464)

<400> SEQUENCE: 6

```
aaa gag att gcc gtg aca att gac gat aag aat gtg att gca tct gtc      48
Lys Glu Ile Ala Val Thr Ile Asp Asp Lys Asn Val Ile Ala Ser Val
  1               5                  10                  15 agt gag tct ttc cat gga gtt gcc ttt gat gcg tct cta ttc tcg ccc      96
Ser Glu Ser Phe His Gly Val Ala Phe Asp Ala Ser Leu Phe Ser Pro
             20                  25                  30 aag ggt cct tgg agc ttt gtt aat att acc tct cca aaa ttg ttc aaa    144
Lys Gly Pro Trp Ser Phe Val Asn Ile Thr Ser Pro Lys Leu Phe Lys
         35                  40                  45 ttg ctg gaa gga ctt tct cct gga tac ttc agg gtt ggc gga acg ttt    192
Leu Leu Glu Gly Leu Ser Pro Gly Tyr Phe Arg Val Gly Gly Thr Phe
```

```
                50                      55                      60
gcc aat tgg ctg ttt ttt gac ttg gac gaa aat aat aag tgg aag gat     240
Ala Asn Trp Leu Phe Phe Asp Leu Asp Glu Asn Asn Lys Trp Lys Asp
65                  70                      75                  80 tat tgg gct ttt aaa gac aaa acc ccc gaa act gcg aca ata aca agg     288
Tyr Trp Ala Phe Lys Asp Lys Thr Pro Glu Thr Ala Thr Ile Thr Arg
                85                      90                      95 aga tgg ctg ttc aga aaa caa aat aat ctg aaa aag gag act ttt gac     336
Arg Trp Leu Phe Arg Lys Gln Asn Asn Leu Lys Lys Glu Thr Phe Asp
            100                     105                     110 gat tta gtg aaa cta aca aag gga agc aag atg aga ttg tta ttc gat     384
Asp Leu Val Lys Leu Thr Lys Gly Ser Lys Met Arg Leu Leu Phe Asp
        115                     120                     125 ttg aat gcc gaa gtg agg act ggt tat gaa att gga aag aag acg aca     432
Leu Asn Ala Glu Val Arg Thr Gly Tyr Glu Ile Gly Lys Lys Thr Thr
    130                     135                     140 tcc act tgg gat tca tcg gag gct gaa aag tta ttt aaa tat tgt gtg     480
Ser Thr Trp Asp Ser Ser Glu Ala Glu Lys Leu Phe Lys Tyr Cys Val
145                     150                     155                 160 tca aaa ggt tac gga gac aat atc gat tgg gaa ctt gga aat gaa ccg     528
Ser Lys Gly Tyr Gly Asp Asn Ile Asp Trp Glu Leu Gly Asn Glu Pro
                165                     170                     175 gac cac acc tca gct cac aat tta act gaa aag cag gtt gga gaa gat     576
Asp His Thr Ser Ala His Asn Leu Thr Glu Lys Gln Val Gly Glu Asp
            180                     185                     190 ttc aaa gca ctg cat aaa gtt tta gag aaa tat cca act ctt aac aag     624
Phe Lys Ala Leu His Lys Val Leu Glu Lys Tyr Pro Thr Leu Asn Lys
        195                     200                     205 gga tcg ccc gtt ggt cca gat gta ggg tgg atg ggc gtc agc tac gtc     672
Gly Ser Pro Val Gly Pro Asp Val Gly Trp Met Gly Val Ser Tyr Val
    210                     215                     220 aag gga ttg gca gac ggg gca ggt gac ctt gta act gct ttt aca cta     720
Lys Gly Leu Ala Asp Gly Ala Gly Asp Leu Val Thr Ala Phe Thr Leu
225                     230                     235                 240 cac caa tat tat ttc gat gga aac acc tct gat gta tca aca tat ctt     768
His Gln Tyr Tyr Phe Asp Gly Asn Thr Ser Asp Val Ser Thr Tyr Leu
                245                     250                     255 gat gcc tca tac ttt aaa aag ctg caa cag ctg ttt gat aaa gtg aaa     816
Asp Ala Ser Tyr Phe Lys Lys Leu Gln Gln Leu Phe Asp Lys Val Lys
            260                     265                     270 gat gtt ttg aaa aat tct cca cat aaa gac aaa cca tta tgg ctt gga     864
Asp Val Leu Lys Asn Ser Pro His Lys Asp Lys Pro Leu Trp Leu Gly
        275                     280                     285 gag aca agt tct gga tgc aac agc ggc aca aaa gat gta tcc gat cga     912
Glu Thr Ser Ser Gly Cys Asn Ser Gly Thr Lys Asp Val Ser Asp Arg
    290                     295                     300 tat gtt tca gga ttt cta aca tta gac aag ttg ggt ctc agt gca gcc     960
Tyr Val Ser Gly Phe Leu Thr Leu Asp Lys Leu Gly Leu Ser Ala Ala
305                     310                     315                 320 aac aat gta aag gtt gtt ata aga cag aca ata tac aat gga tat tat    1008
Asn Asn Val Lys Val Val Ile Arg Gln Thr Ile Tyr Asn Gly Tyr Tyr
                325                     330                     335 ggt ctc ctt gat aaa aac act tta gag cca aat cct gat tac tgg tta    1056
Gly Leu Leu Asp Lys Asn Thr Leu Glu Pro Asn Pro Asp Tyr Trp Leu
            340                     345                     350 atg cat gtt cac aat tct ttg gtc gga aat aca gtt ttt aaa gtt gac    1104
Met His Val His Asn Ser Leu Val Gly Asn Thr Val Phe Lys Val Asp
        355                     360                     365 gtt ggt gat cca act aat aaa acg aga gtc tat gca caa tgt acc aag    1152
```

-continued

```
Val Gly Asp Pro Thr Asn Lys Thr Arg Val Tyr Ala Gln Cys Thr Lys
            370                 375                 380 aca aat agc aaa cac act caa ggc aag tat tac aag ggc tct ttg aca        1200
Thr Asn Ser Lys His Thr Gln Gly Lys Tyr Tyr Lys Gly Ser Leu Thr
385                 390                 395                 400 atc ttt gca ctt aat gtt gga gat gaa gaa gta acg tta aag atc gat        1248
Ile Phe Ala Leu Asn Val Gly Asp Glu Glu Val Thr Leu Lys Ile Asp
                405                 410                 415 caa tac ggc ggt aaa aaa att tat tca tac att ctg aca cct gaa gga        1296
Gln Tyr Gly Gly Lys Lys Ile Tyr Ser Tyr Ile Leu Thr Pro Glu Gly
            420                 425                 430 gga caa ctt aca tca cag aaa gtt ctc ttg aat gga aag gaa ttg aac        1344
Gly Gln Leu Thr Ser Gln Lys Val Leu Leu Asn Gly Lys Glu Leu Asn
            435                 440                 445 tta gtg tct gat cag tta cca gaa cta aat gca gat gaa tcc aaa aca        1392
Leu Val Ser Asp Gln Leu Pro Glu Leu Asn Ala Asp Glu Ser Lys Thr
450                 455                 460 tct ttc acc tta tcc cca aag aca ttt ggt ttt ttt gtt gtt tcc gat        1440
Ser Phe Thr Leu Ser Pro Lys Thr Phe Gly Phe Phe Val Val Ser Asp
465                 470                 475                 480 gct aat gtt gaa gca tgy aar aar                                        1464
Ala Asn Val Glu Ala Cys Lys Lys
                485
```

<210> SEQ ID NO 7
<211> LENGTH: 488
<212> TYPE: PRT
<213> ORGANISM: Hirudinaria manillensis

<400> SEQUENCE: 7

```
Lys Glu Ile Ala Val Thr Ile Asp Asp Lys Asn Val Ile Ala Ser Val
1               5                   10                  15

Ser Glu Ser Phe His Gly Val Ala Phe Asp Ala Ser Leu Phe Ser Pro
                20                  25                  30

Lys Gly Pro Trp Ser Phe Val Asn Ile Thr Ser Pro Lys Leu Phe Lys
            35                  40                  45

Leu Leu Glu Gly Leu Ser Pro Gly Tyr Phe Arg Val Gly Gly Thr Phe
        50                  55                  60

Ala Asn Trp Leu Phe Phe Asp Leu Asp Glu Asn Asn Lys Trp Lys Asp
65                  70                  75                  80

Tyr Trp Ala Phe Lys Asp Lys Thr Pro Glu Thr Ala Thr Ile Thr Arg
                85                  90                  95

Arg Trp Leu Phe Arg Lys Gln Asn Asn Leu Lys Lys Glu Thr Phe Asp
                100                 105                 110

Asp Leu Val Lys Leu Thr Lys Gly Ser Lys Met Arg Leu Leu Phe Asp
            115                 120                 125

Leu Asn Ala Glu Val Arg Thr Gly Tyr Glu Ile Gly Lys Lys Thr Thr
        130                 135                 140

Ser Thr Trp Asp Ser Ser Glu Ala Glu Lys Leu Phe Lys Tyr Cys Val
145                 150                 155                 160

Ser Lys Gly Tyr Gly Asp Asn Ile Asp Trp Glu Leu Gly Asn Glu Pro
                165                 170                 175

Asp His Thr Ser Ala His Asn Leu Thr Glu Lys Gln Val Gly Glu Asp
            180                 185                 190

Phe Lys Ala Leu His Lys Val Leu Glu Lys Tyr Pro Thr Leu Asn Lys
        195                 200                 205

Gly Ser Pro Val Gly Pro Asp Val Gly Trp Met Gly Val Ser Tyr Val
```

```
              210                 215                 220
Lys Gly Leu Ala Asp Gly Ala Gly Asp Leu Val Thr Ala Phe Thr Leu
225                 230                 235                 240

His Gln Tyr Tyr Phe Asp Gly Asn Thr Ser Asp Val Ser Thr Tyr Leu
                245                 250                 255

Asp Ala Ser Tyr Phe Lys Lys Leu Gln Gln Leu Phe Asp Lys Val Lys
                260                 265                 270

Asp Val Leu Lys Asn Ser Pro His Lys Asp Lys Pro Leu Trp Leu Gly
            275                 280                 285

Glu Thr Ser Ser Gly Cys Asn Ser Gly Thr Lys Asp Val Ser Asp Arg
290                 295                 300

Tyr Val Ser Gly Phe Leu Thr Leu Asp Lys Leu Gly Leu Ser Ala Ala
305                 310                 315                 320

Asn Asn Val Lys Val Val Ile Arg Gln Thr Ile Tyr Asn Gly Tyr Tyr
                325                 330                 335

Gly Leu Leu Asp Lys Asn Thr Leu Glu Pro Asn Pro Asp Tyr Trp Leu
            340                 345                 350

Met His Val His Asn Ser Leu Val Gly Asn Thr Val Phe Lys Val Asp
            355                 360                 365

Val Gly Asp Pro Thr Asn Lys Thr Arg Val Tyr Ala Gln Cys Thr Lys
370                 375                 380

Thr Asn Ser Lys His Thr Gln Gly Lys Tyr Tyr Lys Gly Ser Leu Thr
385                 390                 395                 400

Ile Phe Ala Leu Asn Val Gly Asp Glu Glu Val Thr Leu Lys Ile Asp
                405                 410                 415

Gln Tyr Gly Gly Lys Lys Ile Tyr Ser Tyr Ile Leu Thr Pro Glu Gly
                420                 425                 430

Gly Gln Leu Thr Ser Gln Lys Val Leu Leu Asn Gly Lys Glu Leu Asn
            435                 440                 445

Leu Val Ser Asp Gln Leu Pro Glu Leu Asn Ala Asp Glu Ser Lys Thr
        450                 455                 460

Ser Phe Thr Leu Ser Pro Lys Thr Phe Gly Phe Phe Val Val Ser Asp
465                 470                 475                 480

Ala Asn Val Glu Ala Cys Lys Lys
                485

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 8
atcgataaag agattgccgt gac                                    23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 9
tcgcgaaatc gtagcctttg ttg                                    23

<210> SEQ ID NO 10
```

```
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 10
accgtagcgc aggccaaaga gattgccgtg                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
tggcatcgcg tccggtttct ctaacggcac                                    30

<210> SEQ ID NO 12
<211> LENGTH: 87
<212> TYPE: DNA
<213> ORGANISM: Artificial Sequence
<220> FEATURE:
<223> OTHER INFORMATION: Description of Artificial Sequence: Primer

<400> SEQUENCE: 12
cggatccatg aaattcttag tcaacgttgc ccttgttttt atggtcgtat acatttctta   60
catctatgcg aaagagattg ccgtgac                                       87

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 13
ccatggaata cgaagttgta a                                             21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 14
gtagaattca aagagattgc cgtgaca                                       27

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 15
cgccggcgag taatacgaag ttgtaatcgt ag                                 32

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
                       peptide

<400> SEQUENCE: 16

Lys Glu Ile Ala Val Thr Ile Asp Asp Lys Asn Val Ile Ala
 1               5                  10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: 6X His tag

<400> SEQUENCE: 17

His His His His His His
 1               5

<210> SEQ ID NO 18
<211> LENGTH: 178
<212> TYPE: DNA
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: CDS
<222> LOCATION: (21)..(83)
<220> FEATURE:
<221> NAME/KEY: CDS
<222> LOCATION: (139)..(171)

<400> SEQUENCE: 18
ctagataacg agggcaaaaa atg aaa aag aca gct atc gcg att gca gtg gca        53
                     Met Lys Lys Thr Ala Ile Ala Ile Ala Val Ala
                      1               5                  10 ctg gct ggt ttc gct acc gta gcg cag gca tcgatgaatt cgagctcggt          103
Leu Ala Gly Phe Ala Thr Val Ala Gln Ala
             15                  20 acccggggat ccctcgaggt cgacctgcag gcagc gct atg aga gga tcg cat         156
                                      Ala Met Arg Gly Ser His
                                                           25 cac cat cac cat cac taataga                                            178
His His His His His
         30

<210> SEQ ID NO 19
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Met Lys Lys Thr Ala Ile Ala Ile Ala Val Ala Leu Ala Gly Phe Ala
 1               5                  10                  15

Thr Val Ala Gln Ala
             20

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 20

Ala Met Arg Gly Ser His His His His His
 1               5                   10
```

HYALURONIDASE FROM THE *HIRUDINARIA MANILLENSIS* ISOLATION, PURIFICATION AND RECOMBINANT METHOD OF PRODUCTION

The present invention relates to the isolation, purification and characterization of a novel hyaluronidase which derives from the tropical leech *Hirudinaria manillensis*. Therefore, according to this invention the new enzyme is called "manillase". The invention is furthermore concerned with the recombinant method of production of manillase which includes the disclosure of DNA and amino acid sequences as well as of expression vectors and host systems. Finally, the invention relates to the use of manillase for therapeutic purposes, for example, for the treatment of myocardial diseases, thrombotic events and tumors.

Hyaluronic acid or hyaluronan (HA) is a linear unbranched high molecular-weight ($2-6\times10^6$) glycosaminoglycan, composed of a repeating disaccharide structure GlcNAc($\beta$1–4)GlcUA. Its carboxyl groups are fully ionized in the prevailing pH of extracellular fluids, whether normal or pathological. HA belongs together with the chondroitin sulphates, keratan sulfates and heparins to the group of glycosaminoglycans (Jeanloz R. W., Arthr Rheum., 1960, 3, 233–237). In contrast with other unmodified glycosaminoglycans (GAG), it has no sulfate substitution or covalently linked peptide, and its chain length and molecular weight are usually very much greater. HA is ubiquitously distributed in connective tissues and has been found in virtually all parts of the body after introduction of improved fixation method (Hellström S. et al., 1990, *Histochem. J.*, 22, 677–682) and the specific histochemical method with the use of hyaluronan-binding peptides (HABP). It is present during development and maturity in tissues of neuroectodermal origin as well.

The term hyaluronidase refers generally and according to this invention to an enzyme, which acts on hyaluronic acid, irrespective of activity towards other substrates.

Hyaluronidase was first isolated from microorganisms and later from mammalian testis which is now its main source (Meyer K. in *The Enzyme*, 1971, 307).

According to the reaction mechanism, hyaluronidases were divided into three main groups.

In the first group microbial enzymes are combined that act on their substrates by $\beta$-elimination producing $\Delta$4,5-unsaturated disaccharides. The enzyme must therefore be named hyaluronate lyases, EC 4.2.99.1.

The second group, hyaluronoglucosamimidase or testicular-type hyaluronidase (EC 3.2.1.35) acts as an endo-N-acetyl-$\beta$-D-hexosaminidase degrading HA to smaller fragments, in the first place tetrasaccharide with the hexosamine moiety at the free reducing end. Enzymes with similar properties to the testis hyaluronidase have been obtained from tadpoles, snake venom, bee venom, numerous animal tissues, human serum and other sources. It is well know that hyaluronidase from testis has also transglycosylase activity (Weissman B. et al., *J. Biol. Chem.*, 1954, 208, 417–429). The enzymes belonging to this group of hyaluronidases exhibit enzymatic activity not only towards hyaluronate but also towards chondroitin-4-sulfate, chondroitin-6-sulfate, chondroitin and dermatan sulfate.

The third group consists of hyaluronoglucuronidase (EC 3.2.1.36), which acts as an endo-$\beta$-glucuronidase. This enzyme was isolated from the *Hirudo medicinalis* leeches (Yuki H. & Fishman W. H.; *J. Biol. Chem.* 1963, 238, 1877–79) and is absolutely specific for HA. Chondroitin sulfate, dermatan and heparin are not substrates for this hyaluronidase. It degrades only hyaluronic acid to tetrasaccharide with the glucuronic acid at the free reducing end (Linker A. et al., *J. Biol. Chem.*, 1960, 235, 924–27). Opposite to mamalian endo-$\beta$glucosamimidases, heparin has no influence on the activity of this leech hyaluronidase. Therefore, it can be coadministered to a patient together with a heparin and its derivatives extensively used as anticoagulants. A hyaluronic acid specific endo-beta-glucuronidase (called "Orgelase") from species (*Poecilobdella granulosa*) of the sub-family Hirudinariinae (including the genera *Hirudinaria, Illebdella, Poecilodbella, Sanguisoga*) of buffalo leeches was disclosed in EP 0193 330 having a molecular weight of about 28.5. Hyaluronidases have many practical in vivo and in vitro applications. Intravenous administration of hyaluronidase has been proposed for treatment of myocardial infraction (Kloner R. A et al., *Circulation*, 1978, 58, 220–226; Wolf R. A. et al., *Am. J. Cardiol*, 1984, 53, 941–944; Taira A. et al., *Angiology*, 1990, 41, 1029–1036). Myocardial infraction represents a common form of non-mechanical injury; namely severe cell damage and death, caused in this instance by sudden cellular hypoxia. In an experimental myocardial infraction induced in rats (Waldenström A. et al., 1991, *J. Clin. Invest.*, 88, 1622–1628), HA content of the injured (infracted area) heart muscle increased within 24 h to reach nearly three times normal after 3 days, and was accompanied by interstitial oedema. The relative water content of infracted areas also increased progressively reaching a maximum value by day 3 and was strongly correlated with the HA accumulation. The same association of increased HA content with oedema has been observed in experimental heart and renal transplant rejection (Hällgren R. et al., *J. Clin. Invest.*, 1990, 85, 668–673; Hällgren R. et al., *J. Exp. Med.*, 1990, 171, 2063–2076) in rejection of human renal transplants (Wells A. et al. *Transplantation*, 1990, 50, 240–243), lung diseases (Bjermer A. et al., *Brit. Med. J.*, 1987, 295, 801–806) and in idiopathic interstitial fibrosis (Bjermer A. et al., *Thorax*, 1989, 44, 126–131). All these studies provide not only evidence of increased HA in acute inflammation, but demonstrate its part in the local retention of fluid mainly responsible for the tissue swelling and influencing both the mechanical and electrophysiological functions of heart.

These results can explain the mechanism of the action of hyaluronidases used in clinical trials. It was reported that hyaluronidase treatment limited cellular damage during myocardial ischemia in rats, dogs and man (Maclean D. et al. *Science*, 1976, 194, 199). The degradation of the HA can be followed by the reduction of tissue water accumulation, reduction of the tissue pressure and finally better perfusion.

It has been shown that hyaluronidases as well as hyaluronidase containing extracts from leeches can be used for other therapeutic purposes. Thus, hyase therapy, alone or combined with cyclosporine, resulted in prolonged graft survival (Johnsson C. et al. *Transplant Inter*. in press). Hyases ("spreading factor") in the broadest sense are used to increase the permeability of tissues for enhancing the diffusion of other pharmacological agents (e.g. in combination with cytostatics in the treatment of cancer tumors). Furthermore, it could be demonstrated that hyaluronidases are useful in tumor therapy acting as angiogenesis inhibitor and as an aid to local drug delivery in the treatment of tumors, for the treatment of glaucoma and other eye disorders and as adjunct to other therapeutic agents such as local anaesthetics and antibiotics. A general overview of the therapeutic use and relevance is given in the review article of Farr et al. (1997, wiener Medizinische Wochenschrift, 15, p. 347) and literature cited therein. Therefore, there is a need for an active compound such as hyaluronidase. However, the known and available hyaluronidases are either not stable (hyaluronidase from *Hirudo medicinalis*, Linker et. al., 1960, *J. Biol. Chem.* 235, p. 924; Yuki and Fishman, 1963, *J. Biol. Chem.* 238, p. 1877) or they show a rather low specific activity (EP 0193 330, Budds et al., 1987, Comp. Biochem. Physiol., 87B, 3, p. 497). Moreover, none of the known hyaluronidases are available in recombinant form which is an essential prerequisite for intensive commercial use.

This invention discloses now for the first time a new hyaluronidase which was isolated and purified from *Hirudonaria mannilensis* as well as a recombinant version of said enzyme obtained by bioengineering techniques.

Thus, it is an object of this invention to provide a purified protein isolated from the leech species *Hirudinaria manillensis* having the biological activity of a hyaluronidase which is not influenced in its acvtivity by heparin and characterized in that it has a molecular weight of 53–60 kD dependent on glycosylation. The new protein, which is called "manillase", is glycosylated in its native form having a molecular weight of ca. 58 kD (±2 kD) and four glycoforms. However, the non-glycosylated protein is object of the invention as well, obtainable by enzymatic or chemical cleavage of the sugar residues according to standard techniques. The non-glycosylated enzyme of the invention has a molecular weight of about 54 (±2) as measured by SDS-PAGE.

Direct comparison shows that the hyaluronidase disclosed in EP 0193 330 ("orgelase") has under the same conditions a molecular weight of about 28 and contains a lot of impurities such as hemoglobin.

Native manillase according to this invention has a pH optimum of 6.0–7.0, an isoelectric point of 7.2–8.0 and has the amino acid sequence depicted in FIG. 7.

Surprisingly manillase obtained by a preparative purification procedure (see below) has an extremely high specific activity of 100–150, preferably of 110–140 (WHO) kU/mg protein whereas the specific activity of orgelase is about 1,2 kU/mg only. Moreover, orgelase has a lower pH optimum (5.2–6.0) as compared with manillase. Manillase is not influenced, like orgelase, by heparin.

Furthermore it is an object of the invention to provide a process for isolating and purifying manillase comprising the following steps
(i) homogenization of heads of leeches of the species *Hirudinaria manillensis* with an acid buffer and centrifugation,
(ii) ammonium sulfate precipitation of the supernatant of step (i),
(iii) cation exchange chromatography,
(iv) concanavalin A affinity chromatography
(v) hydrophobic interaction chromatography
(vi) affinity chromatography on matrices coated with hyaluronic acid fragments
(vii) gel permeation chromatography, and optionally
(viii) enzymatic or chemical deglycosylation of the purified protein.

The process steps disclosed above guarantee that the protein according to the invention can be obtained with such a high biological enzyme activity. Therefore, it is a further object of this invention to provide a protein having the biological activity of a hyaluronidase which is not influenced in its activity by heparin and having a molecular weight of 53–60 dependent on glycosylation which is obtainable by the process steps indicated above and in the claims and which has preferably a specific enzyme activity of >100 kU/mg protein. The term "unit" relates below and above to "international units" (IU).

The invention discloses a process of making recombinant manillase which includes respective DNA molecules, vectors and transformed host cells.

Therefore, it is an object of this invention to provide a DNA sequence coding for a protein having the properties of native manillase.

It could be also shown, that at least three further clones with slightly different DNA sequences could be selected which are coding for proteins with manillase (hyaluronidase) properties having slightly different amino acid sequences.

The specified clones have the DNA sequences depicted in FIGS. 8, 9 and 10 (upper sequence) which are an object of this invention too as well as expression vectors containing said sequences and host cells which were transformed with said vectors.

In addition, it is object of this invention to provide a recombinant protein with the biological activity of a hyaluronidase and a molecular weight of 55–59 kD dependent on glycosylation having any amino acid sequence depicted in FIGS. 8, 9 and 10 (lower sequence) or a sequence which has a homology to said sequences of at least 80%. The term "manillase" includes all these proteins having the above-specified properties.

The native as well as the recombinant protein(s) may be used as a medicament which can be applied to patients directly or within pharmaceutical compositions. Thus, it is a further aspect of this invention to provide a recombinant or native protein as defined above and below applicable as a medicament and a respective pharmaceutical composition comprising said protein and a pharmaceutically acceptable diluent, carrier or excipient therefor.

The pharmaceutical compositions of the invention may contain additionally further active pharmaceutical compounds of a high diversity. Preferred agents are anticoagulants which do not inhibit or influence the biological and pharmacological activity of the protein according to the invention. Such anticoagulants can be, for example, heparin, hirudin or dicoumarin, preferably, heparin. Thus, it is an object of the present invention to provide a pharmaceutical composition comprising additionally a pharmacologically active compound, preferably heparin.

In connection with use in human or veterinary therapy the protein according to this invention acts preferably as dispersal agent ("spreading" factor) or supports penetration through tissue and skin. Thus, manillase can be used as an adjunct of other substances (such as an local anaesthetic) e.g. in the field of chemotherapy of tumors, for treatment of disorders and diseases with respect to acute myocardial ischemia or infarction, for treatment of glaucoma and other eye disorders, e.g. to improve the circulation of physiological fluids in the eye, for treatment of skin and tissue grafts to remove congestion and improve circulation, as drug delivery system through the skin, membranes, other tissue, as an agent to remove the hyaluronic acid capsule surrounding certain pathogenic microorganisms or certain tumors and cancerous tissues, and as an inhibitor of angiogenesis which can be used as anti-thrombotic and anti-tumor agent.

Therefore, the use of manillase as defined above and below in the manufacture of a medicament for treating especially myocardial, cardiovascular and thrombotic disorders and tumors is an object of this invention.

As used herein, the term "pharmaceutically acceptable carrier" means an inert, non toxic solid or liquid filler, diluent or encapsulating material, not reacting adversely with the active compound or with the patient. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional nontoxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Also other administrations such as oral administration and topical application are suitable. Parenteral compositions and combinations are most preferably adminstered intravenously either in a bolus form or as a constant fusion according to known procedures. Tablets and capsules for oral administration contain conventional excipients such as binding agents, fillers, diluents, tableting agents, lubricants, disintegrants, and wetting agents. The tablets may be coated according to methods well known in the art.

Oral liquid preparations may be in the form of aqueous or oily suspensions, solutions, emulsions, syrups or elixirs, or may be presented as a dry product for reconstitution with water or another suitable vehicle before use. Such liquid preparations may contain conventional additives like suspending agents, emulsifying agents, non-aqueous vehicles and preservatives.

Topical applications may be in the form of aqueous or oily suspensions, solutions, emulsions, jellies or preferably emulsion ointments.

Unit doses according to the invention may contain daily required amounts of the protein according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, enzyme activity (units/mg protein), the object of the treatment, i.e., therapy or prophylaxis and the nature of the disease to be treated.

Therefore, in compositions and combinations such as with anticoagulants like heparin in a treated patient (in vivo) a pharmaceutical effective daily dose of the protein of this invention (manillase) is between about 0.01 and 100 mg/kg body weight (based on a specific activity of 100 kU/mg), preferably between 0.1 and 10 mg/kg body weight. According to the application form one single dose may contain between 0.5 and 10 mg of manillase.

The concentration of e.g. heparin when administered together with manillase is typically 500–4000 U (IU) over one day, however, may be increased or diminished if necessary.

The purification of manillase of the invention was achieved as described in detail in the examples. Table 1 depicts a preparative purification scheme of manillase. Table 2 shows the process of enrichment of the protein according to the invention and Table 3 indicates the comparison of manillase with known leech hyaluronidases.

An enzyme, named manillase, cleaving hayaluronic acid has been isolated from the heads of *Hirudinaria manillensis* leeches and purified to homogeneity. This hyaluronidase was purified using acid-extraction, ammoniumsulfate precipitation, followed by successive chromatography on cation exchanger, Concanavalin A-Sepharose, Propyl-Fractogel, Hyaluronan fragments-Sepharose and Diol-LiChrospher columns. The hyaluronan fragments were prepared by the cleavage of the native hyaluronan with the aid of bovine testes hyaluronidase. After purification and characterization of the fragments, the affinity matrices were prepared as indicated below. Such affinity matrices were applied for the first time for purification of the hyaluronidase. This high-performance chromatography is a technique for fast and efficient purification of hyaluronan binding proteins. The recovery of enzyme activity after each step of purification was reasonably high. The results of the three independent preparative purifications were comparable. They resulted in highly active samples possessing between 20 to 160 kU/mg dependent on the degree of purification. In comparison experiments known hyaluronidases were isolated as indicated in the prior art and their properties were compared with the protein according to this invention (Tab. 3).

The hyaluronidase purified according to the scheme of Tab. 1 differs from other leech hyaluronidases described by other authors. A similar molecular weight was obtained under non-dissociating conditions (any β mercaptoethanol), indicating that manillase is a single subunit enzyme in common with a wide range of hyaluronidase preparations from mammalian sources. This final preparation is a single subunit enzyme (FIG. 1) of apparent molecular weight 58±2 determined with the aid of MALDI, with isoelectric point of 7.2 to 8.0.

TABLE 1

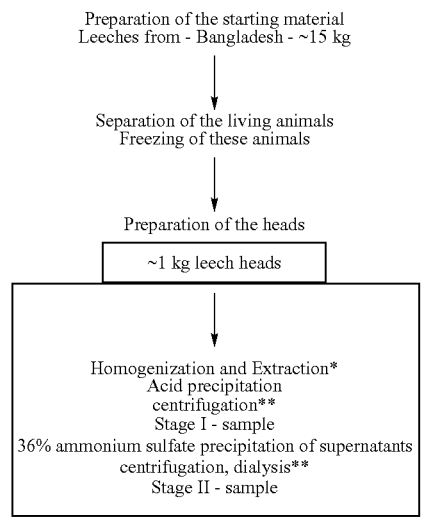

Preparative purification of manillase

TABLE 1-continued

Preparative purification of manillase

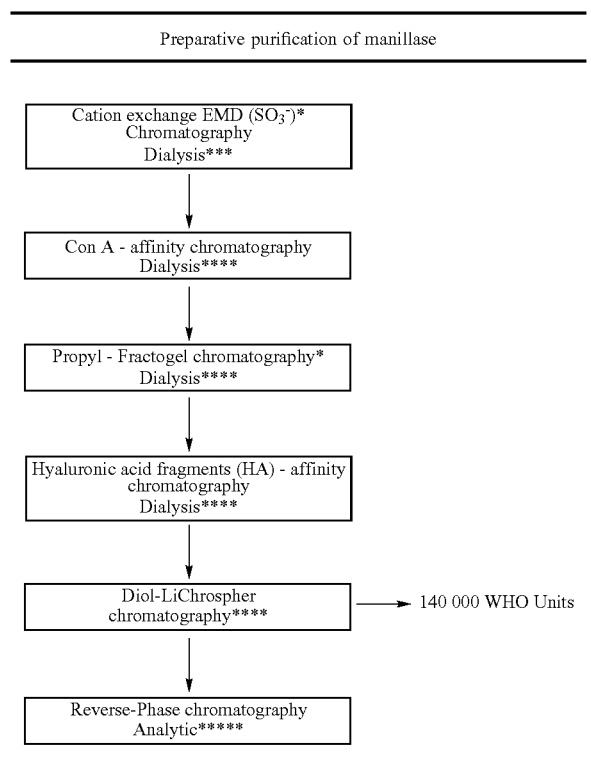

→ 140 000 WHO Units

TABLE 2

Purification of manillase (enrichement) from 1 kg of leech heads

| Step of purification | Total protein Mg | Total activity kU | % recovery | Specific activity U/mg | Purification (fold) |
|---|---|---|---|---|---|
| Stage I supernatant after extraction and acid precipitation | 31700 | 633.3 | 100 | 20 | 1 |
| Stage II supernatant after 36% ammonium sulfate precipitation | 9530 | 443.3 | 70 | 45 | 2.25 |
| Cation exchange chromatography | 426.7 | 332.5 | 52.5 | 770 | 38.5 |
| Con A affinity-chromatography | 41.0 | 166.2 | 26.2 | 4.000 | 200 |
| Propyl-Fractogel chromatography | 11.9 | 133.0 | 21.0 | 11000 | 550 |
| Hyaluronic acid fragments-Sepharose affinity chromatography | 1.9 | 66.4 | 10.5 | 35000 | 1750 |
| Diol-LiChrospher | 0.307 | 33.2 | 5.2 | 108000 | 5400 |

TABLE 3

Comparison of manillase with known leech hyaluronidases

| | "Manillase" Hirudinaria manillens. Invention | Hyaluronidase H. medicinalis comparison experiment | Hyaluronidase H. medicinalis Linker et al.; (J.Biol.Chem, 1960) | "Orgelase" P. granulosa EP 0 193 330 Budds et al. |
|---|---|---|---|---|
| specific activity WHO (IU) units/mg | 140 000 | ~20 000 semipurified | ≤100 | ≤100 |
| homogeneity SDS-PAGE MALDI | 1 protein homogenous 4 glycoforms | Mixture of proteins | no results available | mixture of many proteins main impurity: hemoglobin |
| molecular weight | 58,3 kD ± 2 kD | n. d. | not reported | 28,5 ± 3 kD |
| amino acid sequence | determined | n. d. | not reported | not determined |
| pH optimum | 6.0–7.0 | 6.0–7.0 | not reported | 5,2–6.0 |
| pI | 7.5–8,0 | n. d. | n. d. | n. d. |
| hydrophobicity | binding to Propyl-HIC at 2M ammonium sulfate | no binding to Propyl-HIC at 2M ammonium sulfate | | |
| activity reduction by heparin | no influence | not determined | no influence | no influence |
| Stability | | | | |
| at +4° C. | stable after 7 days ~75% activity retained | Unstable 100% loss of activity after 7 days incubation | | |
| at +37° C. | stable after 7 days ~60% activity retained | Unstable 100% loss of activity after 7 days incubation | | relatively stable |
| stability | stable | Unstable | not reported | not tested |

TABLE 3-continued

Comparison of manillase with known leech hyaluronidases

| | "Manillase" Hirudinaria manillens. Invention | Hyaluronidase H. medicinalis comparison experiment | Hyaluronidase H. medicinalis Linker et al.; (J.Biol.Chem, 1960) | "Orgelase" P. granulosa EP 0 193 330 Budds et al. |
|---|---|---|---|---|
| at +37° C. in the presence of the dog's serum | after 7 days ~100% activity retained | 100% loss of activity after 1 day incubation | | |

The asterisks in the tables mean information on activity determination and biochemical characterization (*-*****).

The methods of activity determination and biochemical characterization used depend of the concentration of manillase in the analyzed samples. Therefore, they were successively extended by the appropriate techniques in the successive steps of purification.

| | |
|---|---|
| * | Activity determination-turbidity reduction test |
| ** | Activity determination-turbidity reduction test Protein content determination ($E_{280}$, Pierce BCA method) SDS-PAGE (SDS-Polyacrylamide Gel Electrophoresis) Hemoglobin determination |
| *** | Activity determination-turbidity reduction test Protein content determination ($E_{280}$, Pierce BCA method) SDS-PAGE-Western Blot (anti human hemoglobin antibody) |
| **** | Activity determination-turbidity reduction test Protein content determination ($E_{280}$, Pierce BCA method) SDS-PAGE-Western Blot anti human hemoglobin antibody, SDS-PAGE-Western Blot anti Con A antibody SDS-PAGE-Western Blot-anti peptide antibodies |
| ***** | MALDI Protein content determination (Pierce BCA method) SDS-PAGE-Western Blot-anti peptide antibodies |

Binding of manillase to Concanavalin A shows that this hyaluronidase is a glycoprotein, whose sugar components are terminated with α-D-mannopyranosyl or α-D-glucopyranosyl and sterically related residues. Manillase-active samples showed two bands with almost identical RF values in SDS-PAGE. Longer SDS-PAGE and different running conditions were used for better separation of the bands. In these experiments two additional, weaker bands could be detected (FIG. 2). The N-terminal part all of them (30 amino acids) was individually sequenced and showed again no difference in the N-terminus. Following deglycosylation with the endo-F-glycosidase (PNGase) it was observed that all four bands resulted in a single band, with a reduction in MW of about 3.

Figure 3:
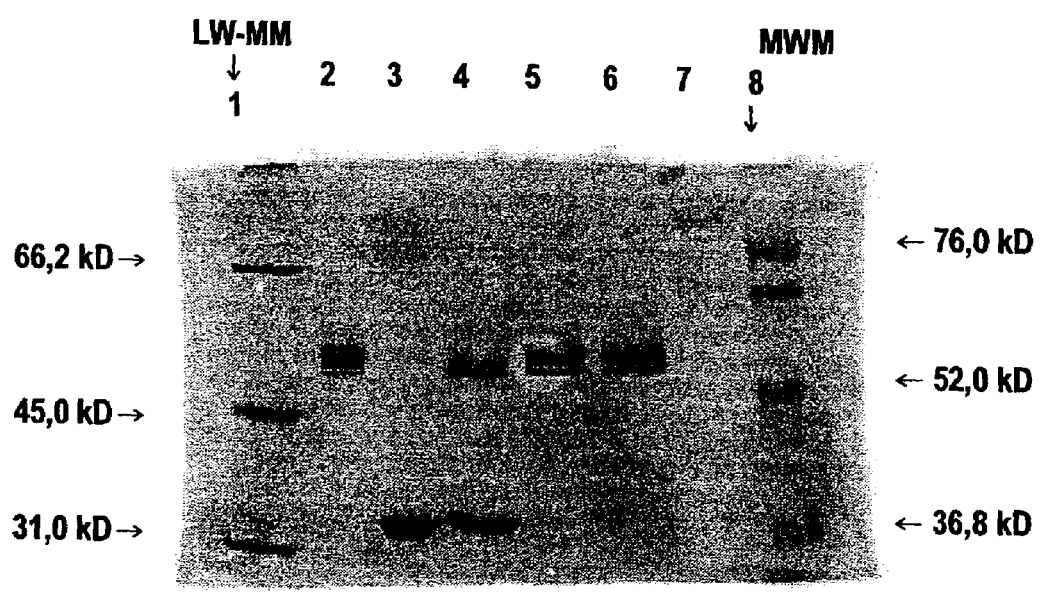

Therefore, it is quite likely that the observed differences in electrophoretic mobility are due to differences in the glycosylation pattern of manillase molecules. The neuramimidase, O-endo-glycosidase and neuramimidase plus O-glycosidase treatments have no influence on the molecular weight of the purified enzyme (FIG. 3). These results have shown that manillase contains at least one N-linked oligosaccharide chain. The O-linked carbohydrate chains could not be detected with the method used.

Figure 4:
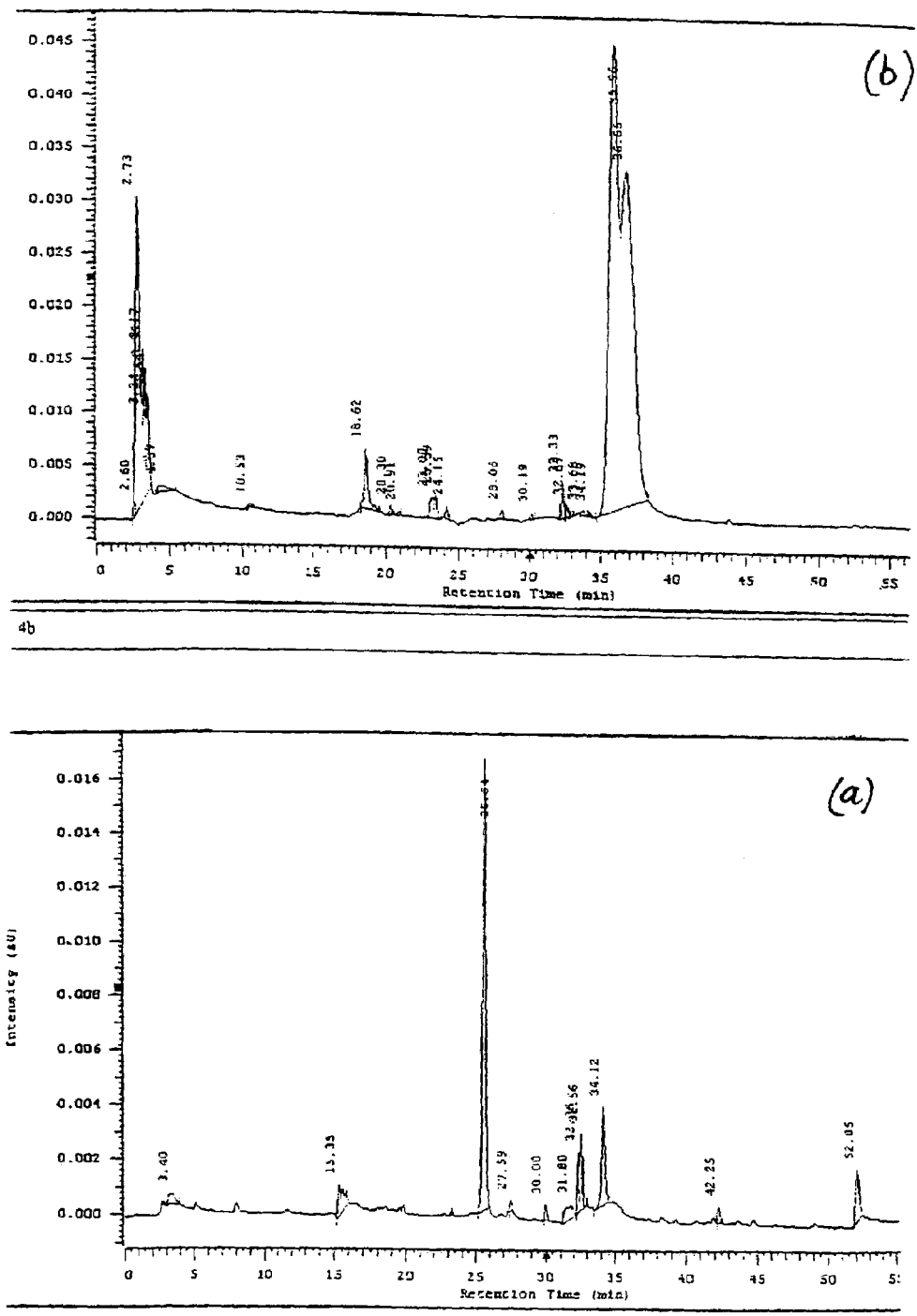

As the concluding purification step, the RP-chromatography was carried out. Although the enzymatic activity could not be detected any more, the salts and peptide protease inhibitors could be removed (FIG. 4). The fractions containing protein were characterized further with the help of MALDI. The molecular weight of manillase determined with the aid of MALDI was 58.3.

Figure 5:
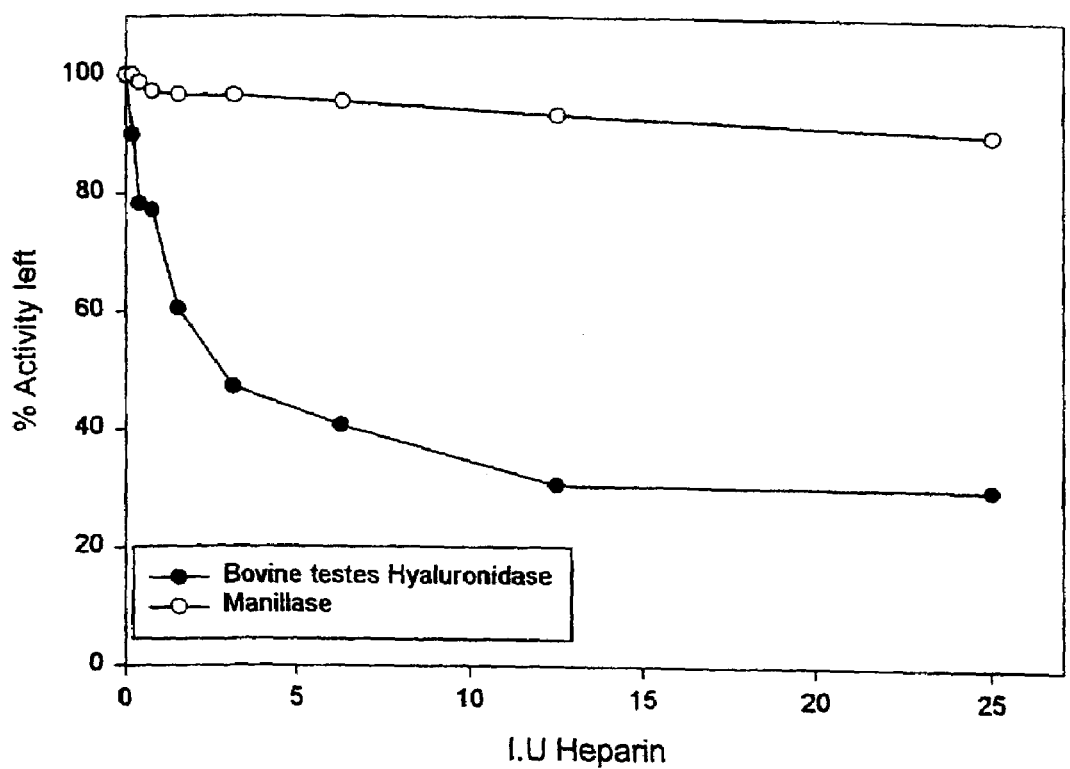
Figure 6A:
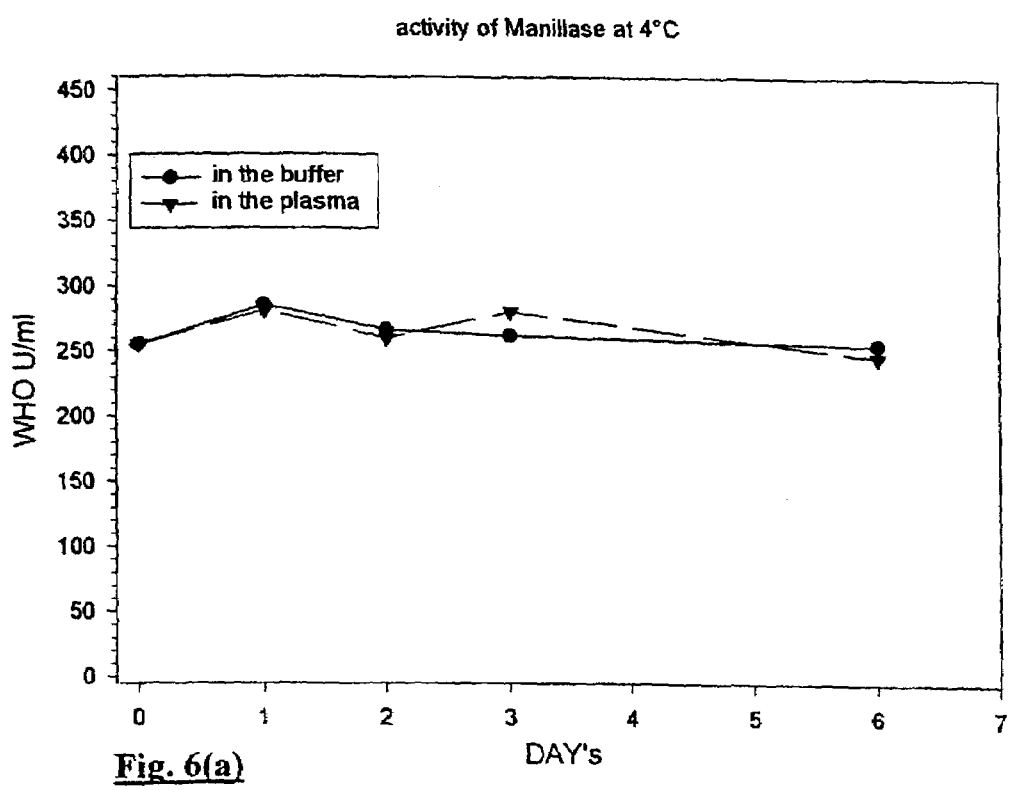
Figure 6B:
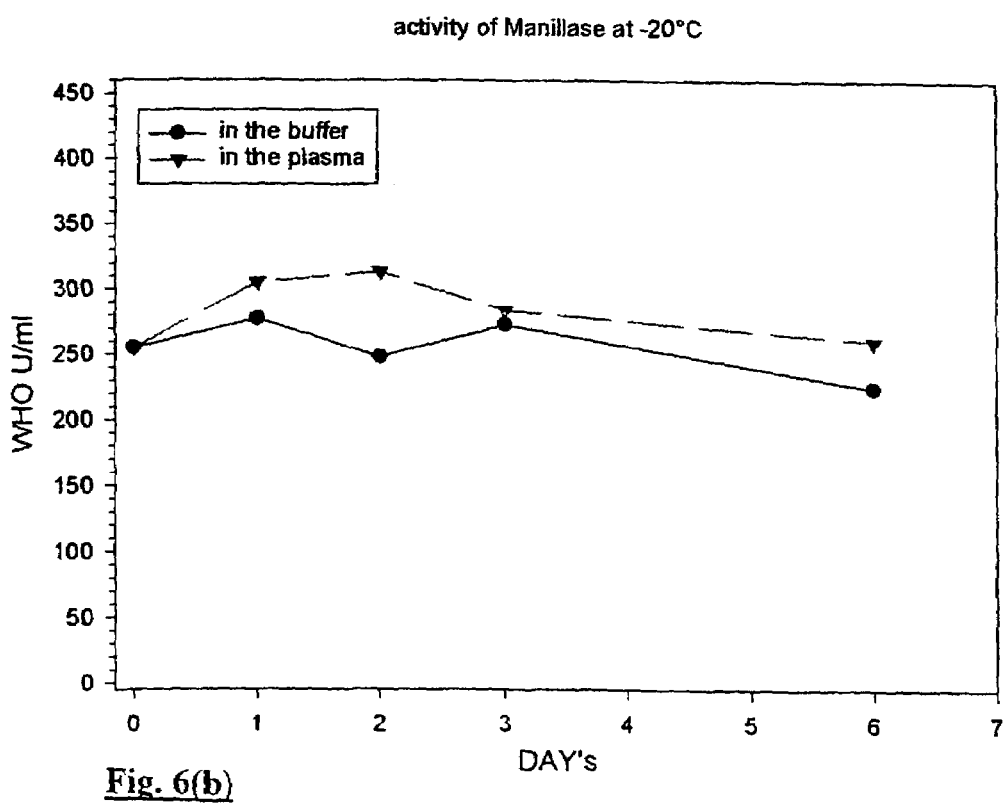
Figure 6C:
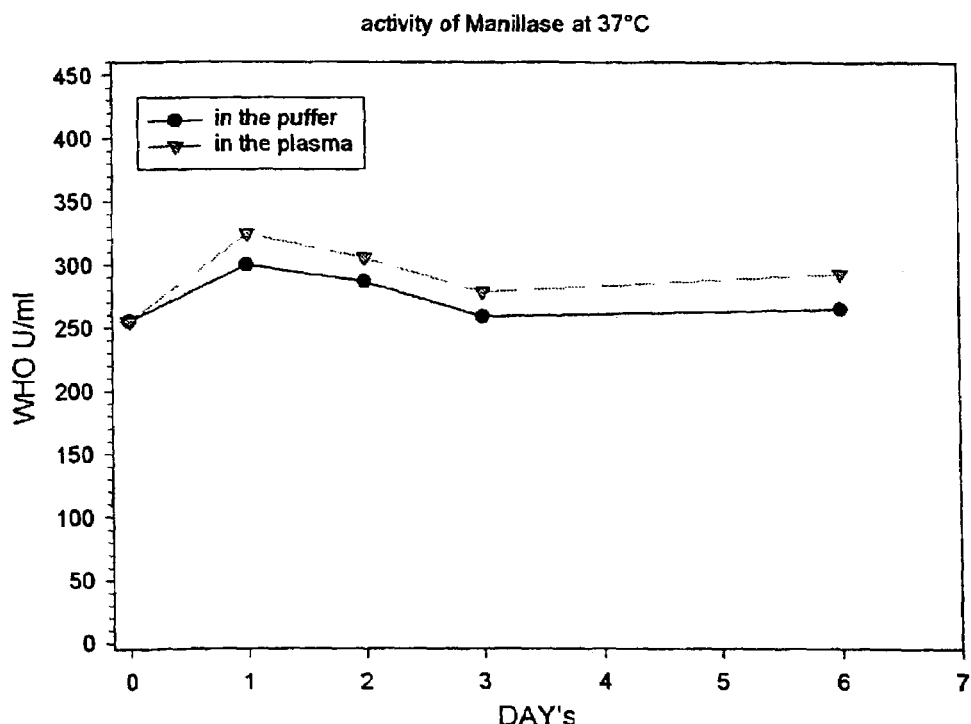
Figure 6D:
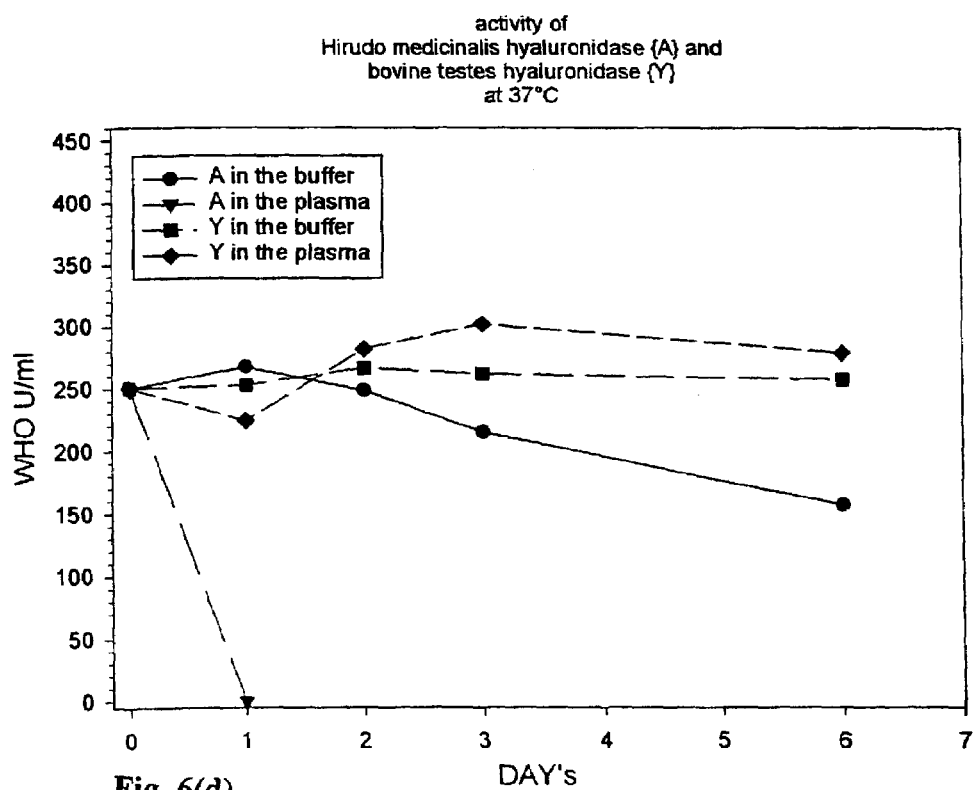

Heparin has no influence on the activity of this hyaluronidase (FIG. 5). Manillase is many fold more stabile than Hirudo medicinalis hyaluronidase (FIG. 6). Moreover, the samples of partly purified manillase showed very high stability in the dogs and rats plasma within the −20 to +37 range.

The preparation of HA-affinity matrices has been described in the literature (Tengblad A., Biochim. Biophys. Acta, 1979, 578, 281–289). This HA-matrix was used for the purification of the cartilage hyaluronate binding proteins or proteoglycan protein-keratan sulfate core (Christner J. E., Anal. Biochem., 1978, 90, 22–32) from the same source. The HA-binding protein (HABP), purified with the aid of this affinity matrix, was used further in histochemical studies concerning the distribution of the hyaluronate receptors (Green S. J. et al., J. Cell Science, 1988, 89, 145–156; Chan F. L. et al., J. Cell. Biol., 1997, 107, 289–301) or hyaluronan (Waldenström A. et al., 1991, J. Clin. Invest, 88,1622–1628; Waldenström A. et al., Eur. J. Clin. Invest, 1993, 23, 277–282) in the tissues.

However, the method of the preparation of this gel developed in our laboratory enables one to produce gels of exactly defined concentration of HA-fragments (1 to 15 mg/ml). This, in turn, enables one to use such gels not only for purification of hyaluronan-binding proteins but also for their separation, by taking advantage of their different affinity to hyaluronan. This selective separation can be controlled by using of HA-fragments of different length. Such separation will enable one to better characterization many receptors of biological relevance (e.g. in oncology).

HA-matrices prepared according to the method described can be applied for the:

1) purification of known HA-binding proteins
2) purification of unknown HA-binding proteins
3) identification of the new HA-binding proteins
4) purification of hyaluronidases HA-fragments obtained by the method described in the present invention can be characterized with the use of modern analytical methods (NMR, MALDI-MS) and applied in the research on protein—protein interactions. Furthermore, these fragments can be used in the research concerning angiogenesis and neovascularization processes

SHORT DESCRIPTION OF THE FIGURES

FIG. 1: SDS-Polyacrylamide Gel Electrophoresis (SDS-PAGE—CBB staining) of the protein standard, manillase sample (after Diol-LiChrospher chromatography).
1—wide range protein standard
2—Manillase, 4 µg
3—Orgelase, 6 µg
4—Hemoglobin, 40 µg FIG. 2: a) SDS-PAGE (CBB staining) and
b) SDS-PAGE—Western blot of four manillase-active samples (lines 3–6) after HA —affinity chromatography. Rabbit P3-2A polyclonal anti-peptide antibody was used in this experiment.

FIG. 3: SDS-PAGE (CBB) of the following samples:
1—LW-MM—low weight molecular marker (BioRad)
2—Manillase
3—N-Glycosidase F (PNGase F)
4—Manillase after treatment with PNGase F
5—Manillase after treatment with O-glycosidase
6—Manillase after treatment with O-glycosidase and neuramimidase
7-O-glycosidase and neuramimidase
8—molecular weight marker (MWM—prestained Bio-Rad)

FIG. 4: Reverse-Phase-Chromatography of
a) Ribonuclease standard
b) manillase sample (specific activity 140 kU/mg)

FIG. 5: Influence of heparin on hyaluronidase activity of manillase (-○-) and bovine testes hyaluronidase (-●-) X-axis: IU heparin; Y-axis: % activity left FIG. 6: Stability measurement of hyaluronidases in buffer and plasma:
(a) manillase (4° C.), (b) manillase (–20° C.)
(c) manillase (37° C.),
(d) bovine testes hyaluronidase (Y) and Hirudo medicinalis hyaluronidase (A)
X-axis: days of incubation; Y-axis: WHO (IU) units FIG. 7: Amino acid sequence of native manillase obtained by sequencing of the isolated and purified protein from Hirudinaria manillensis accordning the invention (corresponds to SEQ ID No. 1)

FIG. 8: Nuclectide (upper lines) and amino acid sequence of a recombinant manillase clone (clone 21); (corresponds to SEQ ID. Nos. 2, 3)

FIG. 9: Nucleotide (upper lines) and amino acid sequence of a recombinant manillase clone (clone 31); (corresponds to SEQ ID. Nos. 4, 5)

FIG. 10: Nucleotide (upper tines) and amino acid sequence of a recombinant manillase clone (clone 31); (corresponds to SEQ ID. Nos. 6, 7)

Figure 11:
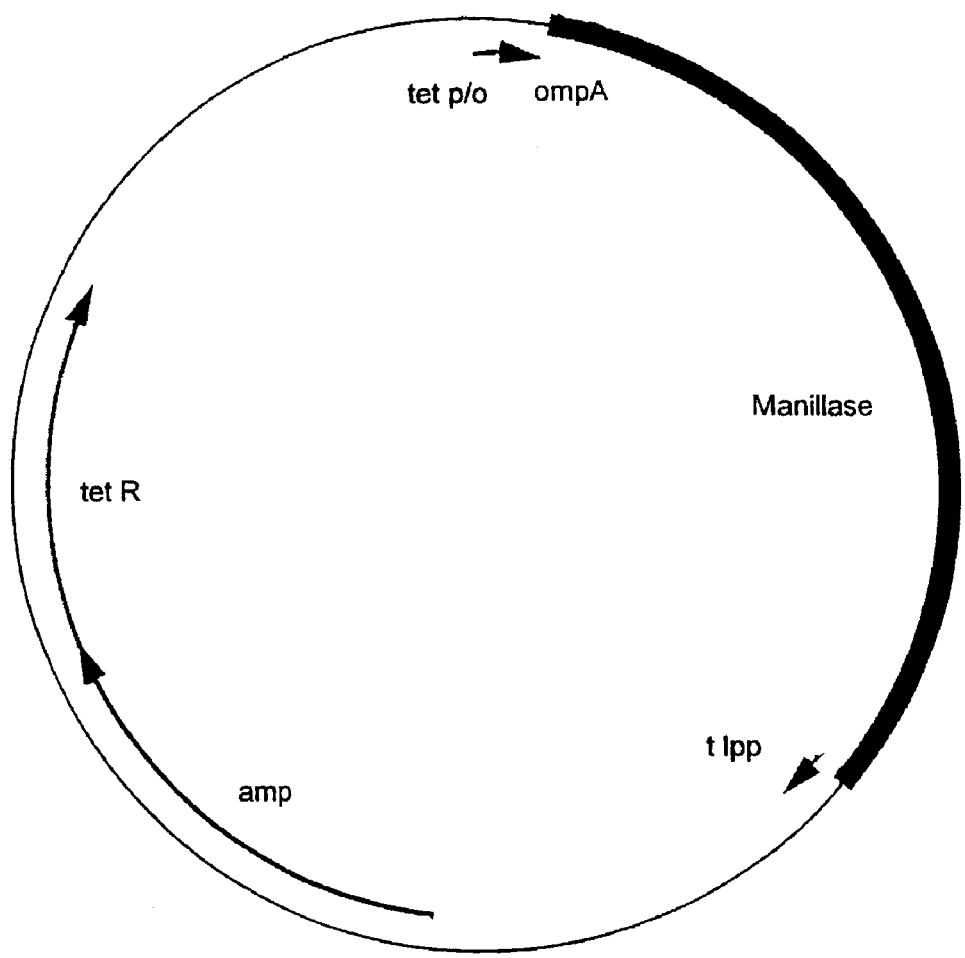

FIG. 11: E. coli expression vector for manillase

Figure 12:
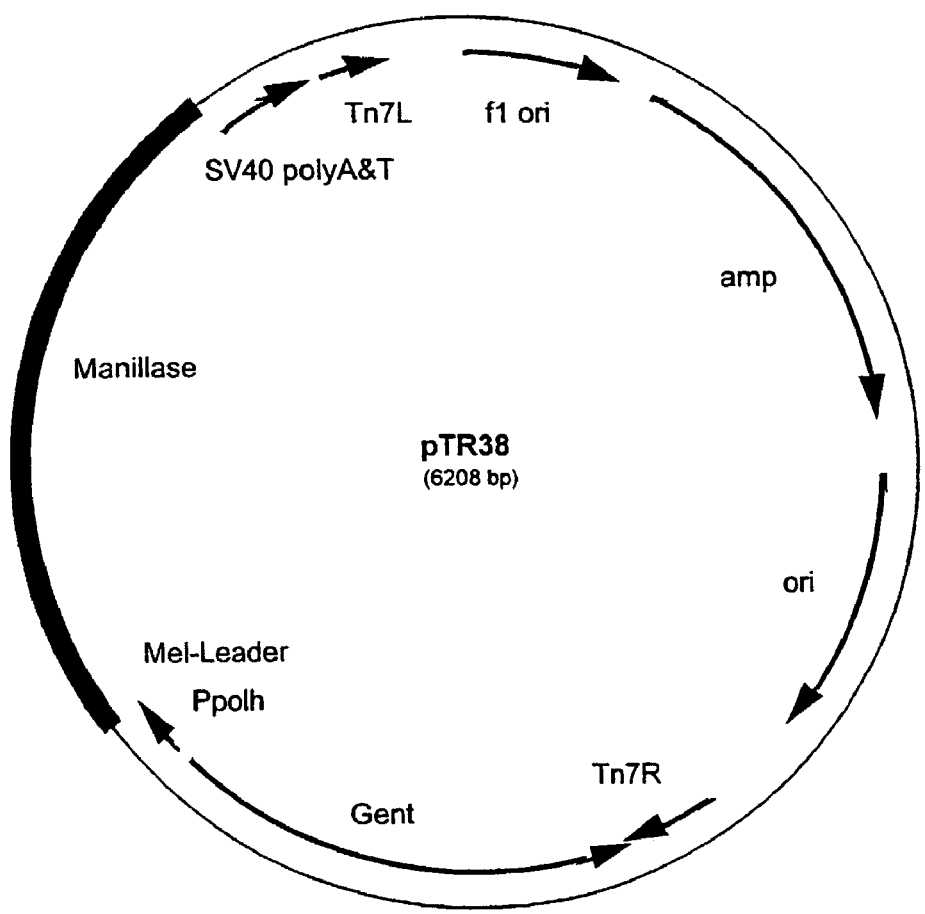

FIG. 12: Baculo donor plasmid for manillase

Figure 13:
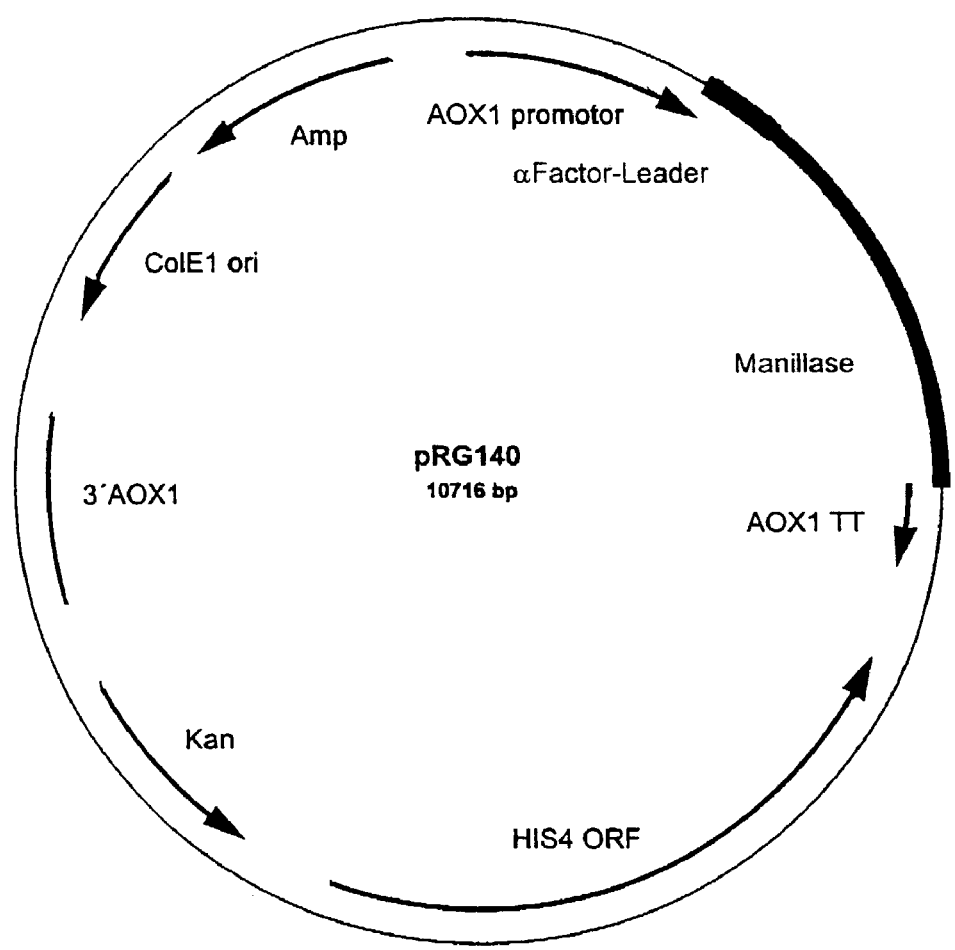

FIG. 13: Yeast expression vector for manillase

The invention is described in detail by the following examples. However, these examples do not limit the invention to the general materials, methods, physical parameters, compounds, biological materials, expression vectors and hosts etc. used in the experiments and indicated in the examples. If not otherwise mentioned standard techniques well known in the prior art and generally available material were used.

EXAMPLE 1

General Remarks

A number of preliminary experiments were carried out using crude extracts of *Hirudinaria manillensis* in order to establish the purification procedure.

The following methods were chosen and verified: ammonium sulfate precipitation procedure, cation and anion exchange chromatography, affinity chromatography with the aid of Heparin-Fractogel, Con A-Sepharose, Hydrophobic Interaction Chromatography (HIC) on Octyl-Sepharose, Propyl- Phenyl-, Butyl-Fractogel, preparative isoelectric focusing and preparative electrophoresis.

The results show that acid and ammonium precipitation, cation exchange, Con A-Sepharose, Propyl-Fractogel HIC and Diol-LiChrospher and Hyaluronic acid fragments-Sepharose (HA-Sepharose) chromatography are suitable for the purification of the manillase. The HA-Sepharose matrix prepared in our laboratory was successfully used for the purification of this glycosidase.

All preparations were carried out in the cold unless otherwise mentioned.

The purification was done according to the scheme shown above (Tab. 1).

EXAMPLE 2

Preparation of the Starting Material for the Purification; Preparation of Leech Heads.

*Hirudinaria manillensis* leeches collected in Bangladesh were immediately shock-frozen and then stored at –40° to –80°. They were decapitated in frozen state, the weight of the heads amounting to ca. 5% of the body.

EXAMPLE 3

Extraction Procedure of Manillase from Leech Heads

In a representative purification, 1 kg of frozen leech heads were homogenized in a Waring Blender with 2500 ml of cold 0.1 M acetic acid buffer pH 4.0 containing 0,025% thimerosal and 17 mg/ml of trehalose (Merck KGaA, Art. No. 1.08216). The homogenate was stirred gently and the following protease inhibitors were added immediately:

| | | |
|---|---|---|
| 1. PMSF | 1.7 mg/ml | 10.0 mM |
| 2.Leupeptin | 10.0 µg/ml | 20.0 µM |
| 3.Pepstatin A | 0.7 µg/ml | 1 µM |
| 4. EGTA | 380.35 µg/ml | 1.0 mM |
| 5.p-APMSF | 40.0 µg/ml | 20.0 µM |

Stirring was continued for 4 hour in the cold and centrifuged at 4900 rpm for 20 minutes. The supernatant solution (supernatant I) was collected and pooled with supernatant II subsequently obtained by extracting the tissues pellet.

The pooled supernatants represent Stage I material.

The procedure is summarized in the following scheme:

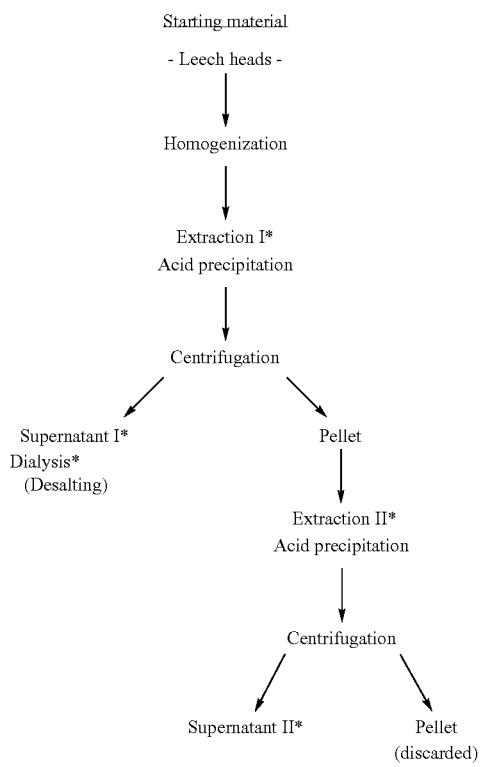

*Activity determination and biochemical characterization of the samples was performed with the aid of activity determination -turbidity reduction test and protein content determination ($E_{280}$, Pierce BCA method, SDS - PAGE).

*Activity determination and biochemical characterization of the samples was performed with the aid of activity determination—turbidity reduction test and protein content determination ($E_{280}$, Pierce BCA method, SDS-PAGE). It was impossible to measure the enzyme activity in the leech homogenate, because of the very high content of hemoglobins (measured with the hemoglobin determination kit, Merck KGaA, 13851) and other proteins. Moreover, the hyaluronidase activity could not be measured in the stage prior to the acid precipitation. The final specific activities (activity per mg of protein) of these extracts were about 10–30 WHO Units. According to SDS-PAGE, the crude extracts contained large amounts of different proteins, the major ones having a molecular weight of ~120, 55–60, 45, 31, 28, 22, 15 and 14-10.

EXAMPLE 4

Ammonium Sulfate Precipitation Procedure of the Stage I Material

Next, the ammonium sulfate precipitation procedure was chosen as the first step of the purification of manillase and resulted in a ~5-fold of enrichment of this enzyme.

Enzymatically inert material was precipitated from Stage I crude extract by adding slowly solid ammonium sulfate (Merck KGaA) to 36% w/v at +4° C. This mixture was stirred for 1 hour and centrifuged. The precipitate was discarded. The supernatant was dialyzed against running de-ionized water overnight, and 24 hours against 20 mM phosphate buffer pH 6.0. The final specific activities of these extracts were about 40–150 WHO Units. According to SDS-PAGE, the stage II extracts contain large amounts of different proteins.

EXAMPLE 5

Cation Exchange Chromatography

The cation exchanger was used in a batch adsorption mode. An enzyme rich dialyzed sample (stage II) was incubated overnight with 1 l Fractogel EMD $SO_3^-$650 (S) cation exchanger, Merck KGaA, Art. No. 16882. After the incubation was finished by centrifugation, the cation exchanger was washed with the buffer, centrifugated again and HPLC-Superformace column was filled with the gel. After washing the column with 20 mM phosphate buffer pH 4.9 the bound proteins were eluted from the column with the same sodium phosphate buffer pH 6.0 containing a linear 0 to 1 M gradient of NaCl. Fractions were collected every 3 min (9 ml) and the absorbance at 280 nm was monitored. Manillase was eluted at 0.15 to 0.18 M NaCl concentrations. The activities and protein contents of all fractions were measured and the fractions were pooled and dialyzed overnight against 20 mM phosphate buffer pH 6.0 containing sodium azide and 17 mg/ml trehalose.

Determination of the concentration of proteins, specific activities of the "pools", and SDS-PAGE analysis were carried out. In spite of very good yields (activity) and high specific activity (WHO activity units per mg of protein, corresponds to IU), a mixture of many proteins was still shown by the results of SDS-PAGE analysis of the samples. The cation exchange chromatography with the aid of Fractogel EMD $SO_3^-$650 (S)® (Merck KGaA, Germany) resulted in a very high purification factor of ~10 to 50. This step is very effective in reducing hemoglobin impurities. Moreover, we have found that the batch procedure was a very useful initial step for handling large volumes of stage II supernatant (5–16 l).

EXAMPLE 6

Concanavalin A-Sepharose Affinity Chromatography

The further purification of the enzyme-rich pools after cation exchanger was done with the aid of Con A lectin affinity chromatography. Commercially available Con A-Sepharose®) from Pharmacia Biotech, Art. 17-0440-01, was washed with an acetic buffer 0.1 M+0.5 M NaCl pH 8.0; 0.1 M boric acid+0.1% Triton X 100 pH 6.0 and finally with 0.1 M acetic buffer+0.5 M NaCl pH 6.0. The sample was dialyzed overnight against 20 mM acetic buffer+0.5 mM NaCl+1 mM $CaCl_2$+1 mM $MgCL_2$ pH 6.0+1 mM $MnCl_2$, applied at room temperature to a 1000 ml Con A column and eluted 2 h with the 510 ml of 100 mM acetic acid buffer+0.5 M NaCl +1 mM $CaCl_2$+1 mM $MgCL_2$ pH 6.0+1 mM $MnCl_2$.

This was followed by desorption with the aid of the same buffer containing 0.5 M methyl-α-D-mannopyranoside. The elution was continuously monitored at 280 nm. The 3 ml fractions that had been collected were assayed for hyaluronidase activity. The active fractions were pooled and dialyzed overnight against 20 mM phosphate buffer pH 6.0 containing sodium azide and 17 mg/ml trehalose. Determination of the concentration of proteins, specific activities of the "pools", and SDS-PAGE analysis was carried out. This step was very effective in removing the rest of hemoglobin.

The Con A chromatography resulted in a 4–10 purification factor. This factor differed, depending on the quality of the starting material.

EXAMPLE 7

Propyl Fractogel Hydrophobic Interaction Chromatography

To hyaluronidase active Con A-pools ammonium sulfate were added to a final concentration of 2 M. The samples were then incubated 1 h at room temperature with 150 ml Propyl-Fractogel EMD Propyl 650 (S)®, Merck KgaA, Germany, Art. No. 1.10085, equilibrated with 0.1 M phosphate buffer pH 7.0, containing 2 M ammonium sulfate. After the incubation was finished the gel was washed twice with the same buffer, and the HPLC-Superformance (2.6 cm×60 cm) column was prepared. The bound proteins were eluted with 0.1 M phosphate buffer pH 7.0. The 6 ml fractions were collected every 3 min, directly dialyzed against de-ionized water (2–3 h) and, then against 20 mM phosphate buffer pH 6.0. The fractions were assayed for hyaluronidase activity. The active fractions were pooled and dialyzed overnight against 20 mM phosphate buffer pH 6.0 containing sodium azide and 17 mg/ml trehalose. The protein and activity determination of the pools was carried out.

The purification factor at this chromatography step was about 3 to 5. A small amount of Con A released from the carrier gel in the previous step was removed together with other protein impurities.

EXAMPLE 8

Preparation of Hyaluronic Acid Oligosaccharide Affinity Column (a) Hydrolysis of Hyaluronan (HA) with Bovine Testes Hyaluronidase Hyaluronic acid, 7 g was dissolved in 1.25 l of 0.1 M sodium acetate buffer containing 0.15 NaCl and 0.5 mM EDTA, pH 5.2 by mixing overnight at 4° C. in the presence of toluene. Thereafter pH of HA containing solution was adjusted to 5.2 and after warming up to 37° C., bovine testes hyaluronidase (Merck KGaA; 700 WHO units/mg) was added. For 7 g of HA, 210 mg of enzyme dissolved immediately before use in 50 ml of the above buffer were used. Hydrolysis was allowed to proceed for 30 min at 37° C. with constant stirring, and terminated by heating for 5 min at 100° C. in a boiling water bath. The reaction mixture was clarified through centrifugation for 30 min at 10 000 g, denatured protein containing sediment was discarded and supernatant filtered through 0.2 µm filter, on which a glass fiber prefilter was placed. Clarified solution containing HA oligosccharides (HAOS) was fractionated by filtration through tree Diaflo ultrafiltration membrane (Amicon) with different molecular cut off values as follows.

(b) Fractionation of HAOS by Ultrafiltration

HAOS—containing solution from the previous step was filtered through 30 YM Diaflo ultrafiltration membrane. Retentate was saved for other studies while filtrate was subjected to the second ultrafiltration through 10 YM Diaflo ultrafiltration membrane. Again, retentate was saved for other studies while the solution passing through 10 YM was subjected to the last ultrafiltration through 3 YM Diaflo membrane. Thereafter, retentate containing HA-OS, about 10 ml of the solution, was used for further purification. This fraction: HAOS 3–10 was purified as follows and further used for coupling to Sepharose.

(c) Purification of HAOS 3–10

HA-OS 3–10 were purified (desalted) on Biogel P2® column. This column (4 cm×100 cm) was packed with Biogel 2 medium®, 200–400 mesh (BioRad), and washed with 5 column volumes of water (Milli Q, Millipore). HAOS 3–10 fraction obtained from the previous step (15 ml; 1.5 g of oligosaccharides) was applied to this column. The column was eluted with water; 15 ml fraction were collected and analyzed for the presence of HA oligosaccharides. Oligosaccharide containing fractions eluted before salts (the latter detected with AgNO3) were combined and concentrated again on 3 YM Diaflo membrane.

(d) Analysis of HAOS 3–10

To determine the coupling efficiency of the Sepharose, gel (the same batch) was washed and suspended in water as to prepare a 50% slurry. From the suspension of Sepharose-HAOS 3–10 conjugate and Sepharose used as a control, 100 µl aliquots were withdrawn in triplicate and added to 2.5 ml of 2.2 N trifluoroacetic acid (TFA, Merck KgaA) in teflon screw capped tube. For hydrolysis, the mixture were flushed with argon and incubated at 100° C. for 16 h. At the end of hydrolysis, samples were dried under nitrogen, re-suspended in water and used for the determination of glucosamine and uronic acid. To determine the extent of uronic acid and glucosamine decomposition for each of the hydrolysis, control samples containing known amounts of UA or GlcNAc were included, and incubated under the same conditions.

Under conditions described above 5, 8, 9, 11 and 15 mg of HAOS 3–10 were coupled per 1 ml of drained Sepharose gel in two independent experiments. This results are based on the UA and glucosamine assays.

(e) Assay Used

The content of the uronic acid in the samples analyzed was determined according to Bitter T. and Muir H. M., *Anal. Biochem.*, 1962, 4, 330–334.

The hexosamine amounts were analyzed with the method of Rondle C. J. M. and Morgan W. T. J., *Biochem. J.*, 1955, 61, 586–593.

EXAMPLE 9

Hyaluronic Aci-d Fragments Sepharose Chromatography (HA-Sepharose Chromatography)

The chromatography matrices containing 8 to 10 mg/ml were prepared as indicated. The enzyme containing sample was dialyzed against 20 mM acetic buffer+0.15 M NaCl pH 4.0 and applied to the 25 ml HA-Sepharose column. After washing with the same buffer, the elution was done with the 20 mM acetic buffer with a 0.15 to 1 M gradient of NaCl.

The 1 ml fractions were tested in the hyaluronidase-activity determination test, pooled, dialyzed overnight against 20 mM phosphate buffer pH 6.0 containing sodium azide and 17 mg/ml trehalose. The protein and activity determination of the pools was carried out. The purification factor of this chromatography step was about 3.

EXAMPLE 10

Diol-LiChrospher Chromatography

A 20 ml active sample dialyzed against Milli-Q-H$_2$O was applied on the Diol-LiChrospher column. The column was then equilibrated with 15 ml Milli-Q-H$_2$O and washed 5 min with 2 ml water. The elution of the active sample was done 15 min with 20 mM acetic buffer pH 5.9 (gradient, 0 to 5 mM NaCl) and 35 min with gradient 20 mM to 100 mM acetic acid buffer pH 5.5 containing 5 mM NaCl. The fractions were assayed for hyaluronidase activity. The active fractions were pooled and dialyzed overnight against 20 mM phosphate buffer pH 6.0 containing sodium azide and 17 mg/ml trehalose. The protein and activity determination of the pools was carried out. The purification factor: 3.

EXAMPLE 11

RP 18E Chromatography

This purification step can be used only as the last one and is aimed to obtain the sample devoid of salts and other protein impurities (e.g. peptide protease inhibitors). The hyaluronidase activity was completely lost, because manillase is not resistance to organic solvents used in this step. Manillase sample was applied to the RP 18e column. The 0.25 ml/min fractions were collected. The elution was done in the presence of 0.1% TFA and, gradient water to 99% of acetonitrile was used. The RP-purified samples can be used directly for amino acid sequencing, MALDI measurement, carbohydrate structure analysis and as standard for purification of other batches of manillase.

EXAMPLE 12

Activity Determination—Turbidity Reduction Test

The hyaluronidase activity determination was done with the turbidity reduction measurements. Commercially available preparations of hyaluronan (isolated from the different animal tissues and fluids, e.g. human cord, rooster comb) and hyaluronidases (endo-β-glucosaminidases from bovine testes, porcine testes, bee venom; lyases from *Streptomyces hyalurolyticus*) were used for establishing suitable activity assay conditions. The endo-β-glucuronidase from *Hirudo medicinalis* was partially purified in our laboratory.

Hyaluronan stock solution (conc. 2 mg/ml) was prepared by dissolving HA in 0.3 M phosphate buffer pH 5.3. This solution was diluted with the same buffer to a concentration of 0.2 mg/ml directly before the test. The enzyme-containing samples were diluted to an appropriate amount of enzyme (0.5–5 WHO units) with 20 mM phosphate buffer containing 0.01% of bovine albumin and 77 mM of NaCl (enzyme dilution buffer). To 0.1 ml of these samples, 0.1 ml hyaluronan (0.2 mg/ml) solution was added, mixed and incubated 45 minutes at 37° C. The test was done in duplicate. The reaction was stopped by dilution with 1.0 ml of albumin reagent (0.1% of albumin dissolved in 80 mM acetic acid/40 mM sodium acetate buffer, pH 3.75). After 10 min incubation at RT or 37° C. the optical density at 600 nm was read and the activity was expressed in WHO (IU) units by comparison (SLT-program) with a standard. The WHO preparation of bovine testicular hyaluronidase (Humphrey J. H., Bull. World Health Org. 1957, 16, 291–294) was used as standard.

EXAMPLE 13

Protein Estimation

The protein content of column eluents was determined by measuring the ultraviolet absorbance of solutions at 280 nm. The protein concentration of the pooled fractions was determined with the aid of Pierce micromethod. The BSA solution was used as a reference protein.

EXAMPLE 14

SDS-Page Electrophoresis

Electrophoresis was done according to Laemmli procedure (Nature, 1970, 227, 680–685). The following gels were used: 4 to 20% gradient or 12.5% separating gels with 4% stacking gel. Samples were subjected to electrophoresis in the presence of sodium dodecyl sulfate and β-mercaptoethanol. Proteins were visualized after staining with Coomassie brilliant blue and/or Silver staining (according to Pharmacia instruction).

EXAMPLE 15

Isoelectric Focusing

To pursue isoelectric focusing studies on the manillase preparation, the protocol provided by supplier (Pharmacia) was adopted. Following focusing, the gel was fixed and silver stained (according to Pharmacia protocol).

EXAMPLE 16

Preparation of Immunoglobin from Immune Sera of Rabbits (Anti-ConA, Anti-Hemoglobin and Anti-Peptide Rabbit Antibodies)

The rabbit sera were raised with the use of the following immunogens: concanavalin A lectin, mixture of hemoglobins and peptide-KLH conjugates. The peptide sequence was identical with that of the 14 amino acid N-terminal part of manillase (KEIAVTIDDKNVIA) (SEQ ID NO: 16). The sera were purified on the Protein A Sepharose (Pharmacia, 17-0780-01) column according to the standard Pharmacia instruction. The purity of the IgG samples were checked with the aid of SDS-PAGE and ELISA-test.

EXAMPLE 17

Western-Immunoblot Assay

Suitable aliquots of the samples and pre-stained protein marker of known molecular weight were subjected to SDS-PAGE as described above. A pre-stained BioRad molecular weight marker was used. The protein was transferred electrophoretically from polyacrylamide gels (0.8 mA/cm2) to immobile polyvinyldifluoride (PVDF) membranes in the presence of transfer buffer for 100 min. The PVDF membrane was incubated with blocking solution (PBS, pH 7.5+ 2% fat free milk) for 1 h at room temperature. Next, the membrane was incubated 2 h at room temperature with the antibody, appropriately diluted with the blocking solution. The membrane was washed with TBS+0.05% Tween 20, pH 7.5, and incubated for 2 h at room temperature with (a second antibody) goat anti-rabbit-alkaline phosphate conjugate, BioRad. The membrane was washed two times with TBS+Tween 20 and incubated 10 min with BCIP alkaline phosphatase substrate solution. Adding a stopping buffer terminated the reaction.

EXAMPLE 18

Amino Acid Sequencing

The sequence of N-terminal 33 amino acid residues of the manillase was obtained by Edman degradation. After SDS-PAGE of manillase-active samples, the bands were transferred onto PDVF membrane, stained with Coomassie Blue, cut-out and sequenced. The same amino sequence was found for the sample obtained after the last purification step with the aid of RP-column chromatography.

EXAMPLE 19 pH Dependence of Enzyme Activity (For Hyaluronidase Isolated from *Hirudinaria manillensis* and *Hirudo medicinalis* Leech Heads)

Samples of hyaluronidase used in this experiment were extracted either from *Hirudinaria manillensis* or *Hirudo medicinalis* leech heads and partially purified with the aid of ammonium sulfate precipitation and cation exchange chromatography. Each sample containing 500 WHO units/ml was incubated at −20° C., +4° C. and 37° C. at a range of pHs from 2.6 to 9.0 (20 mM acetic for pH 2.6 to 5; 20 mM phosphate buffer for pH 5 to 9). The enzyme activity was measured after 1, 2 and 7 days incubation periods. At both acid and alkaline extremes of pH, inhibition of activity to the same extent was observed for both hyaluronidases. However, during longer incubation periods manillase was more stable then *Hirudo medicinalis* hyaluronidase: e.g. after 7 days incubation at pH 7.0 at +4° C. and 37° C.—manillase retained 75% and 60% of the starting activity, respectively. The *Hirudo medicinalis* hyaluronidase incubated at the same conditions was already inactive after 1 day.

EXAMPLE 20

Stability Measurement of Hyaluronidases in the Presence of Dog'S Serum (for Hyaluronidase Isolated from *Hirudinaria manillensis* and *Hirudo medicinalis* Leech Heads)

The 5 kU/ml samples of manillase, *Hirudo medicinalis* and bovine testes hyaluronidase were diluted with dog's or rat's citrated plasma to a final concentration of 250 U/ml. Next, these solutions were incubated at −20° C., +4° C. and +37° C. for 0 to 7 days. The controls containing the same hyaluronidases, diluted in buffer were included in this experiment. Finally, the hyaluronidase activity was measured.

EXAMPLE 21

Contaminating Enzyme Activities

At each stage of the purification procedure for leech hyaluronidase, the preparation was checked for other enzymes capable of degrading protein with the aid of universal protease substrate (Boehringer Mannheim, cat. no. 1080 733) according to Twining S. S. (Anal. Biochem., 1984, 143, 30–34).

EXAMPLE 22

Influence of Heparin on Hyaluronidase Activity

Cleavage of a hyaluronan by hyaluronidases results in the liberation of reducing sugars. The amount of the liberated sugars was measured colorimetrically by the modified method of Park (Park J. & Johnson M.; J. Biol. Chem. 1949, 181, 149). For the measurement of the influence of heparin on the activity of manillase and bovine testes hyaluronidase, two activity determination were carried out: one in the presence of heparin, and second without heparin. Hyaluronidase samples, 25 µl (3.2 WHO units) were incubated 30 min at 37° C. with 25 µl of the heparin (Liquernin, Fa. Hoffmann LaRoche) solution, containing 0 to 24 units of heparin. Then, 50 µl of hyaluronan (2.5 mg/ml) was added and the incubation was continued for 30 min at 37° C. The reaction was terminated by heating for 2 min at 100° C. Next, 100 µl of carbonate-cyanide solution and 100 µl of potassium ferricyanide solution were added to the inactivated digest. The samples were heated in a boiling water bath for 15 min and then cooled in an ice bath. Afterwards, 0.75 µl of ferric ammonium sulfate solution was added to the reaction mixtures. After 15 min incubation at RT, the color developed was measured at 690 nm in a Shimadzu spectrophotometer. Suitable blanks and no-enzyme controls were included in each assay. The expected reducing sugar (glucuronic acid or N-acetyl-glucosamine, 1 to 15 µg) for the type of sample under analysis was used as standard.

EXAMPLE 23

Deglycosylation of the Manillase

The samples of manillase were deglycosylated with the aid of PNGase F enzyme (BioLabs Art. No. 701 L) according to supplier instruction. The de-glycosylation was done under denaturing and native conditions. The O-glycanase, neuramimidase and neuramimidase+O-glycanase treatments were done according to Boehringer Mannheim standard prescriptions. All samples were characterized with the SDS-PAGE and activity determination test.

EXAMPLE 24

Construction of the *E. coli* Expression Vector (FIG. 11)

For expression in *E. coli* we used a modified version of the plasmid pASK75, which carries the tet promoter region. {Skerra, Gene 151, (1994), pp 131–135}. The modification we made by cloning a new linker between the XbaI an Hind III sites. The new linker contains the ompA leader sequence, another multiple cloning site and a 6×His-tag (SEQ ID NO: 17) instead of the strep-tag.

Linker sequence which was cloned in pASK75 (SEQ ID NOS 18–20).

```
     XbaI
119  CTAGATAACG AGGGCAAAAA ATGAAAAAGA CAGCTATCGC GATTGCAGTG GCACTGGCTG
     TATTGC TCCCGTTTTT TACTTTTTCT GTCGATAGCG CTAACGTCAC CGTGACCGAC
                            1▶ MetLysLysT hrAlaIleAl aIleAlaVal AlaLeuAlaG

ClaI      EcoRI    SstI    KpnI SmaI    BamHI
179  GTTTCGCTAC CGTAGCGCAG GC AT CGA TGA ATT CGA GCT CGG TAC CCG GGG
     CAAAGCGATG GCATCGCGTC CG TA GCT ACT TAA GCT CGA GCC ATG GGC CCC

14▶  lyPheAlaTh rValAlaGln Al a

XhoI    SalI     PstI        Eco47III
230  ATC CCT CGA GGT CGA CCT GCA GGC AGC GCTATGAGAGGATCGCATCACCATCACCA
     TAG GGA GCT CCA GCT GGA CGT CCG TCG CGATACTCTCCTAGCGTAGTGGTAGTGGT
                                     1▶ AlaMetArgGlySerHisHisHisHisHi

Hind III
286  TCACTAATAGA
     AGTGATTATCTTCGA
10▶  sHis . . .
```

To construct the expression vector for manillase it was necessary to introduce 5' 'Cla I and 3' Eco47III restriction sites by PCR method. Therefore the two primers 5' ATC GAT AAA GAG ATT GCC GTG AC (SEQ ID NO: 8) and 3' GTT GTT TCC GAT GCT AAA GCG CT (SEQ ID NO: 9) were used. The PCR product first was cloned into the PCR II vector system (Invitrogen) and sequenced.

After expressing and proving the activity of this recombinant manillase in a second PCR reaction the His-tag was removed and the start codon of the manillase gene was directly fused to the omp A leader sequence. The primers for this PCR reaction were:

```
5' ACC GTA GCG CAG GCC AAA GAG ATT GCC GTG
(SEQ ID NO: 10) and

3' CAC GGC AAT CTC TTT GGC CTG CGC TAC GGT
(SEQ ID NO: 11).
```

In a second step the manillase gene was cloned into the modified pASK75 vector using the rectrictionsites 5'ClaI and 3' Eco47111.

EXAMPLE 25

Construction of the Baculo Donor Plasmid
(FIG. 12)

For expression of manillase in the Baculo virus expression system the Bac-To-Bac™ Baculovirus Expression System from Gibco Life Technologies was used. To get a section system the Honeybee melitin leader sequence was fused to the manillase gene and to introduce the restriction sites 5' BamHI and 3' KpnI one single PCR reaction was carried out.

5' Primer:

```
CGG ATC CAT GAA ATT CTT AGT CAA CGT TGC CCT TGT

TTT TAT GGT CGT ATA CAT TTC TTA CAT CTA TGC GAA

AGA GAT TGC CGT GAC (SEQ ID NO: 12)
```

3' Primer:

AAT GTT GAA GCA TAA GGT ACC (SEQ ID NO: 13)

The PCR product was cloned into the PCR II Vector (Invitrogen) and sequenced. Then the Melitin—Manillase Fusion was cloned into the pFastBac vector using the restriction sites 5'BamHI and 3'KpnI (FIG. 12).

EXAMPLE 26

Construction of the Yeast Expression Vector
(FIG. 13)

For expression in yeast we used the *pichia* multi copy expression system (Invitrogen). To construct the expression vector for manillase we used the PCR amplification method of the manillase gene in such a way that compatible restriction ends (5' EcoR I, 3'Not I) are generated for ligation into the appropriate vector (pPIC9K). Therefore the following primers were used:

```
5' GTA GAA TTC AAA GAG ATT GCC GTG ACA (SEQ ID NO: 14)

3' GAT GCT AAT GTT GAA GCA TAA TGA GCG GCC GC
(SEQ ID NO: 15)
```

Before transforming the *Pichia* Speroplasts the expression vector has to be liniarized with Sal I.

EXAMPLE 26

Expression in *E. COLI*

In the expression vector pRG72, which contains the structural gene of Sarastatin fused to the ompA leader sequence, was transformed into W3110 competent cells. The cells were grown to a mid-log phase, and the promoter was then induced by adding 200 μg aTC/l. 1 h thereafter the recombinant manillase could be clearly detected.

EXAMPLE 27

Generation of Recombinant Baculoviruses and Manillase Expression with the Bac-To-Bac Expression System The donor plasmid pTD13 was transformed into DH10Bac competent cells which contain the bacmid with a mini-attTn7 target site and the helper plasmid. The mini-Tn7 element on the donor plasmid ca transpose to the a mini-attTn7 target site on the bacmid in the presence of transposition proteins provided by the helper plasmid. Colonies containing recombinant bacmids were identified by disruption of the lacZ gene. High molecular weight mini-prep DNA prepared from selected E. coli clones containing the recombinant bacmid, and this DNA was then used to transfect insect cells.

Detailed description could be find in the instruction manual of the expression kit.

EXAMPLE 28

Expression in Yeast

To be sure to have integrated the manillase gene the colonies have to be screened for His$^+$Mut$^+$-mutants.

Using a single colony, inoculate 100 ml Medium i a 1 l flask. Growing conditions are: 28–30° C., 250 rpm, up to OD 2–6. To induce expression, first cetrifuge the culture, decant to supernatant and re-suspend the cell pellet in new medium using ⅕ of the original culture volume. Add 100% methanol to a final concentration of 0.5% every 24 hours to maintain induction. After max 6 days supernatant is analyzed by SDS-Page and the activity assay.

What is claimed is:

1. A purified protein isolated from the leech species *Hirudinaria manillensis* having the biological activity of a hyaluronidase which is not influenced in its activity by heparin, characterized in that it has a molecular weight of 53–60 kD dependent on glycosylation.

2. A glycosylated protein according to claim 1 having a molecular weight of 58 (±2) kD.

3. A non-glycosylated protein according to claim 1 having a molecular weight of 54 (2) kD.

4. A protein according to claim 1 having an isoelectric point of 7.2–8.0.

5. A protein according to claim 1 having the amino acid sequence given in FIG. 7 (SEQ ID NO:1).

6. A protein according to claim 1 having a specific enzymatic activity of >100 kU/mg protein.

7. A protein of claim 1 having the amino acid sequence of SEQ ID NO: 3.

8. A protein of claim 1 having the amino acid sequence of SEQ ID NO: 5.

9. A protein of claim 1 having the amino acid sequence of SEQ ID NO: 7.

10. A recombinant protein with the biological activity of a hyaluronidase and a molecular weight of 55–59 kD dependent on glycosylation having an amino acid sequence with at least 94% homology to SEQ ID NO:3.

11. A protein of claim 10, having at least 96% homology to SEQ ID NO: 3.

12. A protein of claim 10, having at least 97% homology to SEQ ID NO: 3.

13. A process for isolating and purifying the protein of claim 1 comprising:
   (i) homogenization of heads of leeches of the species *Hirudinaria manillensis* with an acid buffer and centrifugation,
   (ii) ammonium sulfate precipitation of the supernatant of step (i),
   (iii) cation exchange chromatography,
   (iv) concanavalin A affinity chromatography,
   (v) hydrophobic interaction chromatography,
   (vi) affinity chromatography on matrices coated with hyaluronic acid fragments, and
   (vii) gel permeation chromatography.

14. A process of claim 13, further comprising:
   (viii) enzymatic or chemical de-glycosylation of the purified protein.

15. A protein having the biological activity of a hyaluronidase which is not influenced in its activity by heparin and having a molecular weight of 53–60 kD dependent on glycosylation, obtainable by the process steps of claim 13.

16. A protein according to claim 15 having a specific enzymatic activity of >100 kU/mg protein.

17. A DNA sequence coding for a protein of claim 1.

18. A DNA sequence coding for a protein of claim 15 comprising a nucleotide sequence depicted in FIG. 8 (SEQ. ID NO: 2), FIG. 9 (SEQ. ID NO: 4) or FIG. 10 (SEQ ID NO: 6).

19. A recombinant protein having the biological activity of a hyaluronidase encoded by any a DNA sequence of claim 18.

20. An expression vector comprising a DNA sequence of claim 17.

21. A host cell suitable for the expression of a protein of claim 19 which was transformed with a vector comprising a DNA sequence for a protein comprising a nucleotide sequence depicted in FIG. 8 (SEQ. ID NO: 2), FIG. 9 (SEQ. ID NO: 4) or FIG. 10 (SEQ ID NO: 6).

22. A pharmaceutical composition comprising a protein of claim 1 and a pharmaceutically acceptable diluent, carrier, or excipient therefor.

23. A pharmaceutical composition comprising the protein of claim 7 and a pharmaceutically acceptable diluent, carrier or excipient therefor.

24. A pharmaceutical composition according to claim 22, further comprising heparin.

25. A method of treating myocardial, cardiovascular and thrombotic disorders and tumors in a subject, comprising administering a protein of claim 1 to said subject.

* * * * *

UNITED STATES PATENT AND TRADEMARK OFFICE
CERTIFICATE OF CORRECTION

PATENT NO. : 7,049,124 B1
APPLICATION NO. : 10/009500
DATED : May 23, 2006
INVENTOR(S) : Kordowicz et al.

It is certified that error appears in the above-identified patent and that said Letters Patent is hereby corrected as shown below:

Column 49, line 18, reads "(2)" should read -- (±2) --

Signed and Sealed this

Twelfth Day of December, 2006

JON W. DUDAS
*Director of the United States Patent and Trademark Office*